US012613209B2

(12) United States Patent
Rajabipour et al.

(10) Patent No.: US 12,613,209 B2
(45) Date of Patent: Apr. 28, 2026

(54) EMBEDDED SENSOR SYSTEM FOR MEASUREMENT AND MONITORING OF THE PORE SOLUTION ELECTRICAL RESISTIVITY IN CONCRETE MATERIALS AND STRUCTURES

(71) Applicant: The Penn State Research Foundation, University Park, PA (US)

(72) Inventors: Farshad Rajabipour, State College, PA (US); Andrew Drach, Austin, TX (US); Nima Kargah-Ostadi, Alexandria, VA (US); Gopakumar Kaladharan, State College, PA (US); Kostiantyn Vasylevskyi, Nashua, NH (US); Borys Drach, Las Cruces, NM (US)

(73) Assignee: The Penn State Research Foundation, University Park (PA)

( * ) Notice: Subject to any disclaimer, the term of this patent is extended or adjusted under 35 U.S.C. 154(b) by 110 days.

(21) Appl. No.: 18/559,400

(22) PCT Filed: May 11, 2022

(86) PCT No.: PCT/US2022/028730
§ 371 (c)(1),
(2) Date: Nov. 7, 2023

(87) PCT Pub. No.: WO2022/240963
PCT Pub. Date: Nov. 17, 2022

(65) Prior Publication Data
US 2024/0230568 A1     Jul. 11, 2024

Related U.S. Application Data

(60) Provisional application No. 63/186,960, filed on May 11, 2021.

(51) Int. Cl.
| | | |
|---|---|---|
| *G01N 27/04* | (2006.01) | |
| *G01N 27/20* | (2006.01) | |
| *G01N 33/38* | (2006.01) | |

(52) U.S. Cl.
CPC ........... *G01N 27/041* (2013.01); *G01N 27/04* (2013.01); *G01N 27/20* (2013.01); *G01N 33/383* (2013.01); *G01N 27/048* (2013.01)

(58) Field of Classification Search
CPC .... G01N 27/041; G01N 27/20; G01N 33/383; G01N 27/048; G01N 27/04
USPC ......................................................... 324/693
See application file for complete search history.

(56) References Cited

U.S. PATENT DOCUMENTS

| | | | |
|---|---|---|---|
| 6,007,904 A | 12/1999 | Schwotzer | |
| 2003/0016009 A1* | 1/2003 | Li ........................ | G01N 27/023 |
| | | | 324/239 |
| 2004/0124858 A1* | 7/2004 | Srinivasan ............. | G01N 27/04 |
| | | | 324/693 |

(Continued)

*Primary Examiner* — Raul J Rios Russo
(74) *Attorney, Agent, or Firm* — Riverside Law LLP

(57) ABSTRACT

The present invention relates in part to an embedded sensor for measuring the electrical resistivity or conductivity of pore solution in concrete materials and structures, wherein the sensor comprises a synthetic nanoporous ceramic, or nanoporous polymer, or cementitious material with controlled pore size. The present invention also relates to a method of measuring the electrical resistivity of pore solution in a concrete sample or a concrete structure.

20 Claims, 9 Drawing Sheets

(56) References Cited

U.S. PATENT DOCUMENTS

| | | | | |
|---|---|---|---|---|
| 2005/0193800 A1* | 9/2005 | DeBoer | ................ | G01N 27/128 |
| | | | | 73/1.06 |
| 2006/0163088 A1* | 7/2006 | Xu | ....................... | G01N 27/404 |
| | | | | 205/793 |
| 2007/0126433 A1 | 6/2007 | Theophanous | | |
| 2009/0028213 A1 | 1/2009 | Kund | | |
| 2009/0321280 A1* | 12/2009 | Kimble | .................. | G01N 17/02 |
| | | | | 204/406 |
| 2010/0000346 A1 | 1/2010 | Just | | |
| 2015/0226718 A1 | 8/2015 | Holt | | |
| 2016/0061806 A1 | 3/2016 | Reid | | |
| 2019/0187085 A1* | 6/2019 | Brom-Verheyden | ........................ | |
| | | | | G01N 27/07 |
| 2020/0360892 A1 | 11/2020 | Ma | | |
| 2021/0063336 A1 | 3/2021 | Ghods | | |

* cited by examiner

EMBEDDED SENSOR SYSTEM FOR MEASUREMENT AND MONITORING OF THE PORE SOLUTION ELECTRICAL RESISTIVITY IN CONCRETE MATERIALS AND STRUCTURES

CROSS-REFERENCE TO RELATED APPLICATIONS

This application is a 35 U.S.C. § 371 National Phase Application claiming priority to International Application No. PCT/US2022/028730, filed May 11, 2022, which claims priority to U.S. Provisional Patent Application No. 63/186,960 filed May 11, 2021, each of which is incorporated herein by reference in its entirety.

STATEMENT REGARDING FEDERALLY SPONSORED RESEARCH OR DEVELOPMENT

This invention was made with government support under Contract No. 6913G621P800050 awarded by the United States Department of Transportation/Volpe National Transportation Systems. The Government has certain rights in the invention.

BACKGROUND OF THE INVENTION

Concrete is the most widely produced human-made material in the world. The per-capita concrete production in the United States is estimated at 2 tons/year (van Oss, H. G., Cement statistics and information, USGS Minerals Information, 2017), and globally the industry is worth $500 billion (Ready-mix concrete market size and forecast by application, by region, and trend analysis from 2013-2024, Grand View Research, 2016).

In-situ measurement of the electrical resistivity/conductivity of concrete pore solution allows for health monitoring of vital concrete structures (such as bridges, pavements, marine structures, etc.) via: 1) monitoring changes in the internal chemistry of the system due to cement hydration, pozzolanic reaction, penetration of aggressive ions (such as chlorides and sulfates), or carbonation; and 2) quantifying, at any given age, the microstructural and transport properties of concrete such as formation factor, ion diffusivity, and water permeability (F. Rajabipour, Ph.D. Dissertation, 2006, Purdue University, West Lafayette, Indiana; F. Rajabipour, et al., 2004 in: Advances in Concrete through Science and Engineering, a RILEM International Symposium, Evanston, IL; F. Rajabipour, et al., TRB Annual Meeting 2007, Paper #07-1765, Transportation Research Board, Washington, DC; F. Rajabipour, J. Weiss, ACI Special Publication: SP 252-1, 2008, American Concrete Institute (ACI)).

Additionally, development of Performance Engineered concrete Mixtures (PEM) according to AASHTO PP84-20 (American Association of State Highway and Transportation Officials (2021) "AASHTO PP 84-20: Standard Practice for Developing Performance Engineered Concrete Pavement Mixtures.") requires rapid evaluation of the transport properties and formation factor of concrete to predict and ensure the quality and durability of the concrete that is being placed and constructed (PEM test for transport: Resistivity/formation factor test, 2020, National Concrete Pavement Test Center, University of Iowa). The transport properties and formation factor (F) of concrete are determined by simultaneous measurements of the resistivity/conductivity of concrete and resistivity/conductivity of the concrete pore solution. As such, reliable measurement of the latter is of paramount importance for quality control (QC) and quality assurance (QA) of concrete.

In June 2021, the U.S. Department of Transportation (U.S. DOT) Small Business Innovation Research (SBIR) Program awarded a Phase I contract to Callentis Consulting Group, LLC (with the Pennsylvania State University as the subcontractor) for the development of an in-situ pore solution resistivity/conductivity sensor, highlighting the significance and commercialization potential of such sensors within the broad concrete industry in the United States and internationally. As stated in the corresponding SBIR solicitation by the Federal Highway Administration (FHWA), "The opportunity for commercialization [of a pore solution conductivity sensor] in the U.S. is high. There are many [transportation] agencies that are transitioning to electrical property evaluation of their concrete mixtures, and this solution would be a simple way to implement the evaluation and correlate measurements with durability performance" (SBIR Program, 2021, U.S. Department of Transportation). An in-situ pore solution resistivity/conductivity sensor could also be implemented in commercial concrete construction sector for structures exposed to penetration and damage by aggressive salts (e.g., parking structures, coastal structures, etc.). Following a successful proof of concept report from Phase I, the USDOT SBIR program awarded a Phase II contract to the same team (Callentis Consulting Group, LLC as the prime and the Pennsylvania State University as the subcontractor) to further develop, verify and demonstrate the prototype sensor system.

A concrete's formation factor (F) is used to assess the concrete's transport properties and durability. The F factor has been shown to be an important parameter in service-life prediction models to predict chloride ion penetration and corrosion, permeability, and water absorption of concrete. The F factor is defined as the ratio of the electrical resistivity of the bulk concrete mixture over the electrical resistivity of the concrete pore solution. Two concrete mixtures with the same bulk resistivity can have very different porosity and durability, which can only be reliably discerned and quantified by having an accurate measurement of the pore solution resistivity of the two mixes. There are existing standard test methods to measure the bulk concrete resistivity in a laboratory and in the field, but there are no standard equipment or test methods for measuring the pore solution resistivity in the field. In-situ measurement of the electrical resistivity of the pore solution along with the resistivity of bulk concrete allows for qualification and approval of concrete mix designs before construction, quality control (QC) and quality acceptance (QA) of concrete batches delivered and placed during construction, service-life prediction, and health monitoring of vital concrete infrastructure such as bridges, pavements, and marine structures. The technology may be used by asset owners and/or commissioners of concrete structures (e.g., state Departments of Transportation, US Department of Defense) and may be ideally suited for their contractors and subcontractors who are involved in concrete mix design, production, placement, construction, quality control, and service-life monitoring and inspection.

There is a need in the art for an embedded sensor or system of embedded sensors for measuring the electrical resistivity or conductivity of pore solution in concrete materials and structures. The present invention satisfies this need.

3

SUMMARY OF THE INVENTION

Some embodiments of the invention disclosed herein are set forth below, and any combination of these embodiments (or portions thereof) may be made to define another embodiment.

In one aspect, the present invention relates to a pore solution resistivity/conductivity sensor, the sensor comprising: a first electrode; a second electrode spaced from and opposite said first electrode; a nanoporous matrix between the first and second electrode; said first and second electrodes being situated on a common axis or parallel axes and each having electrical leads connected thereto and wherein said electrical leads extend through and outside the nanoporous matrix. In one embodiment, the nanoporous matrix has a cylindrical shape with a curved surface along its vertical extent. In one embodiment, the nanoporous matrix has a cuboidal shape. In one embodiment, the sensor further comprises a continuous-body sensor housing. In one embodiment, the sensor further comprises a sensor for measuring temperature and relative humidity.

In one embodiment, the nanoporous matrix has an average pore size smaller than 20 nm in diameter. In one embodiment, the nanoporous matrix comprises a nanoporous ceramic material. In one embodiment, the nanoporous ceramic matrix comprises a transition metal oxide, aluminum oxide, germanium oxide, silicon oxide, boron nitride, clay, silica, titania, germania, zirconia, alumina, mullite, or a combination thereof. In one embodiment, the nanoporous matrix further comprises a monomolecular film coating. In one embodiment, the monomolecular material comprises an organosilane.

In one embodiment, the nanoporous material comprises a nanoporous polymer material. In one embodiment, the nanoporous polymer material comprises an ethylene-based polymer, a propylene-based polymer, an epoxy resin, a polyurethane, a silicone, an un-saturated ester, a phenolic resin, or combinations, mixtures, copolymers, and/or block copolymers thereof. In one embodiment, the nanoporous polymer material comprises polydimethylsiloxane (PDMS), polyurethane, polymethylmethacrylate (PMMA), polystyrene, cellophane, polyethylene, Polytetrafluoroethylene, poly(propylene), poly(vinyl chloride) (PVC), poly(hydroxyethyl methacrylate) (pHEMA), poly(ethylene terephthalate), polyether ether ketone (PEEK), polyether sulfone (PES), Nylon 6.6, high density polyethylene (HDPE), ultra high molecular weight polyethylene (UHMWPE), Highly cross-linked polyethylene (HXPE), Poly(ethylene glycol) (PEG), expanded PTFE (ePTFE), Poly(vinylpyrrolidone) (PVP), Poly(styrene-b-isobutylene-b-styrene) (SIBS), ethylene tetrafluoroethylene (ETFE), fluorinated ethylene propylene (FEP), tetrafluoroethylene (TFE), perfluoroalkoxy alkanes (PFA), fluorinated polypropylene (FLPP), low-density polyethylene (LDPE), polypropylene (PP), polyvinyl chloride (PVC), or combinations, mixtures, copolymers, or block copolymers thereof. In one embodiment, the nanoporous polymer matrix further comprises a metal oxide coating. In one embodiment, the metal oxide coating is selected from the group consisting of $Al_2O_3$.

In one embodiment, the nanoporous matrix comprises a covalent organic framework. In one embodiment, the covalent organic framework is selected from the group consisting of COF-1, COF-5, COF-6, COF-8, COF-10, COF-11A, COF-14A, COF-16A, COF-18A, COF-42, COF-43, COF-66, COF-366, TP-COF, NiPc-PBBA COF, CTF-0, CTF-1, HTTP-DBP COF, ZnPc-Py COF, ZnPc-DPB COF, ZnPc-NDI COF, ZnPc-PPE COF, TpPa-1, or TpPa-2, TpPa-NO$_2$,

4

TpBD-(NO$_2$)$_2$, TpBD-Me$_2$, TpPa-F$_4$, TpBD-OMe$_2$, TpBD, DhaTph COF, TAPB-TFP COF, iPrTAP-TFP, TAPB-TFPB, ILCOF-1, DAAQ-TFP COF, TAPB-PBA COF, HPB COF, HCB COF, H$_2$P-COF, Ph-An-COF, Tp-Azo COF, TP-PirDI COF, Py-Azine COF, CS COF, CuP-SQ COF, CuP-Ph COF, CuP-TFPh COF, Star-COF, CuPc-COF, CoPc-COF, NiPc BTDA COF, ZnP-COF, Ppy-COF, 1-S COF, 1-Se COF, 1-Te COF, T-COF 1, T-COF 2, T-COF 3, T-COF 4, NTU-COF-1, NTU-COF-2, APTES-COF-1, FCTF-1 COF, TRITER-1, TDCOF-5, BLP-2 COF, TpTP-H, TpTP-OEt, TpTP-OMEG, TpTP-ODEG, TpTP-OTEG, and combinations thereof.

In one embodiment, the nanoporous matrix comprises a nanoporous cementitious material. In one embodiment, the nanoporous cementitious material comprises a hardened cement paste made with cement and water at w/cm<0.42 and cured to maturity by means of ambient moist curing, steam curing, or autoclave curing. In one embodiment, the nanoporous cementitious material further contains supplementary cementitious materials (SCM) and/or chemical admixtures. In one embodiment, the nanoporous cementitious material comprises a geopolymer formed from an alumino-silicate precursor material selected from the group consisting of metakaolin, calcined clay, natural pozzolan, volcanic ash, fly ash, ground bottom ash, and slag cement.

In one aspect, the present invention relates to a method for measuring the electrical resistance of concrete pore solution, the method comprising the steps of: embedding the pore sensor in a concrete sample or concrete structure; actuating the sensor with one or several levels of alternating or direct electrical currents; and measuring the resistance between the first electrode and the second electrode.

In one aspect, the present invention relates to a sensor described herein, which is embedded inside a concrete sample or within a concrete structure.

BRIEF DESCRIPTION OF THE DRAWINGS

The following detailed description of various embodiments of the invention will be better understood when read in conjunction with the appended drawings. For the purpose of illustrating the invention, illustrative embodiments are shown in the drawings. It should be understood, however, that the invention is not limited to the precise arrangements and instrumentalities of the embodiments shown in the drawings.

DETAILED DESCRIPTION

Figure 1:
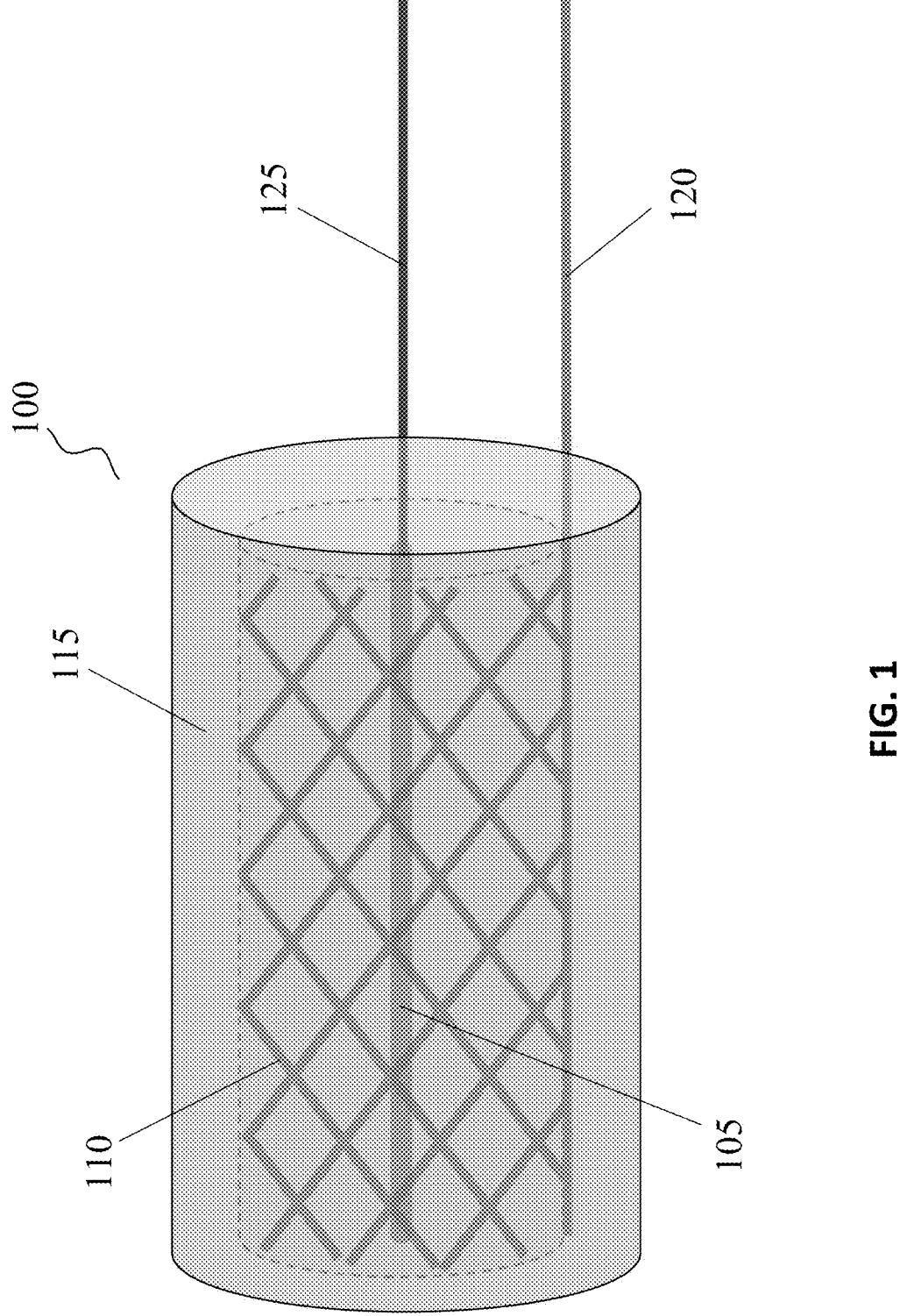
FIG. 1 depicts an exemplary coaxial electrode sensor according to an aspect of the present invention.

The present invention can be understood more readily by reference to the following detailed description, examples, drawings, and claims, and their previous and following description. However, it is to be understood that this invention is not limited to the specific compositions, articles, devices, systems, and/or methods disclosed unless otherwise specified, and as such, of course, can vary. While aspects of the present invention can be described and claimed in a particular statutory class, such as the composition of matter statutory class, this is for convenience only and one of skill in the art will understand that each aspect of the present invention can be described and claimed in any statutory class.

It is to be understood that the Figures and descriptions of the present invention have been simplified to illustrate elements that are relevant for a clear understanding of the present invention, while eliminating, for the purpose of clarity, many other elements found in sensors, composite materials and methods of making. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

While the present invention is capable of being embodied in various forms, the description below of several embodiments is made with the understanding that the present disclosure is to be considered as an exemplification of the invention and is not intended to limit the invention to the specific embodiments illustrated. Headings are provided for convenience only and are not to be construed to limit the invention in any manner. Embodiments illustrated under any heading or in any portion of the disclosure may be combined with embodiments illustrated under the same or any other heading or other portion of the disclosure.

Any combination of the elements described herein in all possible variations thereof is encompassed by the invention unless otherwise indicated herein or otherwise clearly contradicted by context.

Unless otherwise expressly stated, it is in no way intended that any method or aspect set forth herein be construed as requiring that its steps be performed in a specific order. Accordingly, where a method claim does not specifically state in the claims or description that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of embodiments described in the specification. It is to be understood that both the foregoing general description and the following detailed description are exemplary and explanatory only and are not restrictive.

All publications mentioned herein are incorporated herein by reference to disclose and describe the methods and/or materials in connection with which the publications are cited.

As used herein, each of the following terms has the meaning associated with it in this section. Unless defined otherwise, all technical and scientific terms used herein generally have the same meaning as commonly understood by one of ordinary skill in the art to which this invention belongs.

The articles "a" and "an" are used herein to refer to one or to more than one (i.e. to at least one) of the grammatical object of the article. By way of example, "an element" means one element or more than one element.

As used herein, the term "about" will be understood by persons of ordinary skill in the art and will vary to some extent depending on the context in which it is used. As used herein when referring to a measurable value such as an amount, a temporal duration, and the like, the term "about" is meant to encompass variations of +20% or +10%, more preferably +5%, even more preferably +1%, and still more preferably +0.1% from the specified value, as such variations are appropriate to perform the disclosed methods.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range. Further, for lists of ranges, including lists of lower preferable values and upper preferable values, unless otherwise stated, the range is intended to include the endpoints thereof, and any combination of values therein, including any minimum and any maximum values recited.

As used herein, the term "concrete" refers to a product formed from a mixture of cement, water, and aggregates and may include supplementary cementitious materials (SCM) and chemical admixtures. The term "concrete product" can include products such as, but not limited to, concrete, stucco, fiber cement composites, cement paste, and mortar. This includes pre-cast, cast-in-place, and ready-mixed concrete materials and products. Herein, use of the term "fresh concrete" is consistent with its use in the art. Fresh concrete includes a freshly made concrete (from 0 hours) that is still wet and extends to that stage of concrete in which the concrete can be molded and it is in plastic (deformable) state. "Concrete setting" refers to conversion from plastic to hardened state and can take as long as 6 hours, or even as long as 18 hours.

The term "cement" refers to any hydraulic cement as defined by ASTM C219-20(a).

The concrete ingredients can be any concrete ingredients known to a person of skill in the art. In one embodiment, the concrete ingredients comprise one or more of: cement, water, coarse aggregates, fine aggregates, supplementary cementitious materials (SCMs), mineral fillers, chemical admixtures, fibers, and combinations thereof, as defined by ASTM C125-21a or otherwise known to a person of ordinary skill in the art.

The term "electrical resistivity" or "resistivity" refers to a shape/size-independent material property describing the resistance of that material to passage of electricity. The term "electrical conductivity" or "conductivity" is the mathematical inverse of resistivity (conductivity=1/resistivity).

The term "polymer," as used herein, refers to a polymeric compound prepared by polymerizing monomers, whether of the same or a different type. The generic term polymer thus embraces the term homopolymer (employed to refer to polymers prepared from only one type of monomer, with the understanding that trace amounts of impurities can be incorporated into the polymer structure), and the term interpolymer as defined hereinafter. The term "interpolymer," as used herein, refers to polymers prepared by the polymerization of at least two different types of monomers. The generic term interpolymer includes copolymers (employed to refer to polymers prepared from two different monomers), and polymers prepared from more than two different types of monomers.

The term "ethylene-based polymer," as used herein, refers to a polymer that comprises a majority amount of polymerized ethylene monomer (based on weight of the polymer) and, optionally, may contain at least one comonomer.

The term "propylene-based polymer," as used herein, refers to a polymer that comprises a majority amount of polymerized propylene monomer (based on weight of the polymer) and, optionally, may comprises at least one comonomer.

The present invention is based in part on the unexpected result that nanoporous sensors can be used for direct measurement of conductivity/resistivity of concrete pore solutions.

Devices of the Invention

In one aspect, the present invention relates in part to a pore solution conductivity/resistivity sensor, the sensor comprising a first electrode; a second electrode spaced from and opposite said first electrode; and a nanoporous material or matrix positioned between the first electrode and the second electrode; said first and second electrodes each having electrical leads connected thereto. While numerous embodiments of the present invention are described herein, it should be appreciated that the sensors may include placement of one or more electrodes fully or partially within the nanoporous matrix, on the surface of the nanoporous matrix, or any combination thereof. There is no limitation to the size or shape of the nanoporous material, and there is no limitation to the further integration of the sensors into any desired housing framework or system, for example for use in concrete samples or structures.

In one embodiment, the sensor further comprises means for developing an alternating current across said electrodes. In one embodiment, the sensor further comprises a means for producing a potential field between said electrodes. In one embodiment, the sensor's ends are coated with an insulating coating to further prevent current leakage outside of the sensor. In one embodiment, parts of the surface of the central electrode or the surface of the circumferential electrode may be covered by an annular electrical insulator.

In one aspect, the present invention relates to a sensor housing wherein in the pore solution conductivity sensor is partially encapsulated such that one or more parts of the sensor body is in direct contact with the surrounding concrete and one or more parts is insulated away from the surrounding concrete.

In one aspect, the present invention relates to a sensor packaging wherein the sensor body is inserted into a housing to hold the sensor.

In one embodiment, the sensor packaging is a placement mechanism to easily embed the sensor in concrete cylinders or structures. In one embodiment, the sensor packaging is a placement mechanism to plug the package into a sensor holding frame to embed the sensor in concrete cylinders or structures.

In one aspect, the present invention relates in part to a sensor holding frame, the holding frame comprising a wiring used to interrogate the sensor through the wire leads, a recessed channel to guide the wiring from a central location on the frame to a position on the edge of the frame, and a protective dome designed to prevent damage to the sensor.

In one aspect, the present invention relates in part to a sensor package shipping container, the container having a sealable interior volume and comprising a pore solution resistivity sensor, and a simulated pore solution.

In one embodiment, the shipping container is a container with a lid that may be affixed and removed. In one embodiment, the shipping container is a vacuum-sealable bag.

In one aspect, the present invention relates to a concrete sample or concrete structure comprising a sensor described herein. It should be appreciated that any use of the term sample or structure is not limiting in volume or shape. In some embodiments, the sensor is added during the formation (placement) of the concrete. In one embodiment, the sensor becomes a permanent feature of the formed concrete. In one embodiment, the sensor is embedded inside concrete and allow in-situ measurement of pore solution electrical resistivity (or pore solution electrical conductivity) of concrete. In one embodiment, a concrete structure may include more than one pore solution sensor. In one embodiment, a concrete structure may include the pore solution sensor, a relative humidity/moisture sensor, and a temperature sensor.

In one aspect, the present invention relates to the electrical control and/or interrogation of the system described herein. In one embodiment, the system comprises a computing device. In one embodiment, the computing device is powered via an electrical power source. In one embodiment, the computing device is connected to lead wires to interrogate the sensor via the sensor electrodes. In one embodiment, the computing device is connected directly to the sensor electrodes. In one embodiment, the computing device is external to the concrete sample or structure. In one embodiment, the computing device is located within the concrete sample or structure. In one embodiment, the computing device can provide electrical current to the electrodes. In one embodiment, the computing device can read electrical signal from the electrodes. In one embodiment, the computing device can process electrical signal from the electrodes. In one embodiment, the computing device can record and store electrical signal from the electrodes. In one embodiment, the computing device can report the stored electrical signal from the electrodes to an external system and/or operator of system.

In one embodiment, the interrogation of the system is performed by the use of a commercially available interrogation device. In one embodiment, the commercial interrogation device can excite the sensor at pertinent AC frequency ranges. In one embodiment, the commercial interrogation devices are used in both the lab-setup and field measurement of the sensors.

Example Interrogation Devices:
  I. For Lab applications:
    a. Giatec RCON meter
    b. Hioki IM3536 LCR Meter
    c. Instek LCR-6002 Precision LCR Meter
    d. Keysight E4980AL/032 e. Solartron 1260A Impedance Analyzer f. Etc.

II. For field applications:

a. Proseq Resipod Concrete Resistivity Meter 40 Hz including BR measurement kit b. B&K Precision 880 Handheld LCR c. Keysight U1733C Handheld LCR Meter d. Extech 380193 LCR Meter e. Etc.

In one aspect, the present invention relates to the data collection from the sensors embedded in concrete samples or structures. In one embodiment, the automatic data collection from sensors embedded in concrete samples or structures is independent actuation of the sensors and wireless communication of the measurements to a data acquisition unit. In another embodiment, the measurements are taken with one or more lead wires (e.g., an electrical plug) that are accessible from the outside surface. In one embodiment, the sensors are interrogated with a handheld device, which also serves as a power source.

In one aspect, the interrogator device measures for electrical resistivity for a sensor that is saturated in pore solution of the surrounding concrete. In one embodiment, the interrogator device is adjusted for known geometry factor of the sensor. The formation factor of the sensor matrix $(F_s)$ is known from the pre-calibration process at the manufacturing facility. The measured electrical resistivity of the saturated sensor divided by the formation factor results in the electrical resistivity of the concrete pore solution. In one embodiment, the calculations including formation factor and electrical resistivity of the saturated sensor is programmed into the interrogation device such that a technician will read the final measurement.

In one aspect, the interrogator device is a battery powered device used for actuating the sensors. In one embodiment, the battery-powered interrogator device actuates the sensor with DC current. In one embodiment, the interrogator device also connects to a battery-powered DC to AC inverter. In one embodiment, the battery-powered DC to AC inverter is included with the sensor package. In one embodiment, the sensor package is equipped with a Bluetooth transmitter to wirelessly control the power actuation of the sensor and also transmit data to a Bluetooth receiver on the job site. In one embodiment, one or more Bluetooth transmitters connected to sensors broadcasts data to a Bluetooth receiver, wherein the receiver is connected to a computing device that saves the data and transmits to a cloud-based server.

In one aspect, the present invention relates to a system with electrical circuitry for enabling the invention described herein. In one embodiment, the system comprises an electrical circuit with electrical components. In one embodiment, the electrical circuit is forming a connection between a computing system and a plurality of electrodes. In one embodiment, the electrical circuit is producing electrical current sent to the electrodes. In one embodiment, the electrical circuit comprises one or more operational amplifiers. In one embodiment the electrical circuit is amplifying a signal received from the electrodes. In one embodiment, the electrical circuit is performing a signal filtering of one or more electrical signals. In one embodiment the electrical circuit is performing mathematical computations of one or more electrical signals.

In one aspect, the present invention relates to a computing device with operational software enabling the invention described herein. In one embodiment, the computing device of the system comprises a software executing the instructions provided herein and may be stored on a non-transitory computer-readable medium, wherein the software performs some or all of the steps of the present invention when executed on a processor. In one embodiment, the computing device comprises a software executing the necessary steps for analog to digital conversion of one or more electrical signals. In one embodiment, the software correlates the electrical signals to spatial data of the system. In one embodiment, the software correlates the electrical signals to temporal data of the system. In one embodiment, the software correlates the system, signals and data to a geo-location. In one embodiment, the system comprises a software executing the steps for producing a user interface for a graphical representation of the system data.

Sensors

As mentioned previously, the present invention relates in part to a pore solution conductivity/resistivity sensor for use in concrete samples or structures. The sensors include first and second electrodes separated by a material, such as a nanoporous matrix as described elsewhere herein. The material or nanoporous matrix may be of any desired size or shape. The electrodes may be positioned on the surface of the matrix, partially embedded within the matrix, or fully embedded within the matrix. Electrical leads are connected to the electrodes and allow for connectivity to external electrical lines or sources. The electrodes may be positioned in any configuration with respect to the nanoporous matrix and each other as is desired, provided that there is at least a portion of the nanoporous matrix between the electrodes. For example, the electrodes may be positioned opposite each other, along parallel axes, coaxially, tangentially, radially, circumferentially, or the like.

Now referring to FIG. 1, shown is an exemplary sensor 100 comprising a coaxial electrode arrangement within the sensor to minimize current leakage while providing abundant contact surface between the sensor body and the surrounding concrete to facilitate chemical equilibrium. Electrode 105 is at the center of the cylinder while electrode 110 is a mesh at the internal cylinder's circumference. The nanoporous matrix 115 is depicted as the cylindrical region surrounding the electrodes. The sensor's matrix is extended beyond the mesh electrode to provide protection. Electrical lead 120 extends outside of nanoporous matrix 115 and is in contact with electrode 105. Electrical lead 125 extends outside of nanoporous matrix 115 and is in contact with electrode 110.

Figure 2:
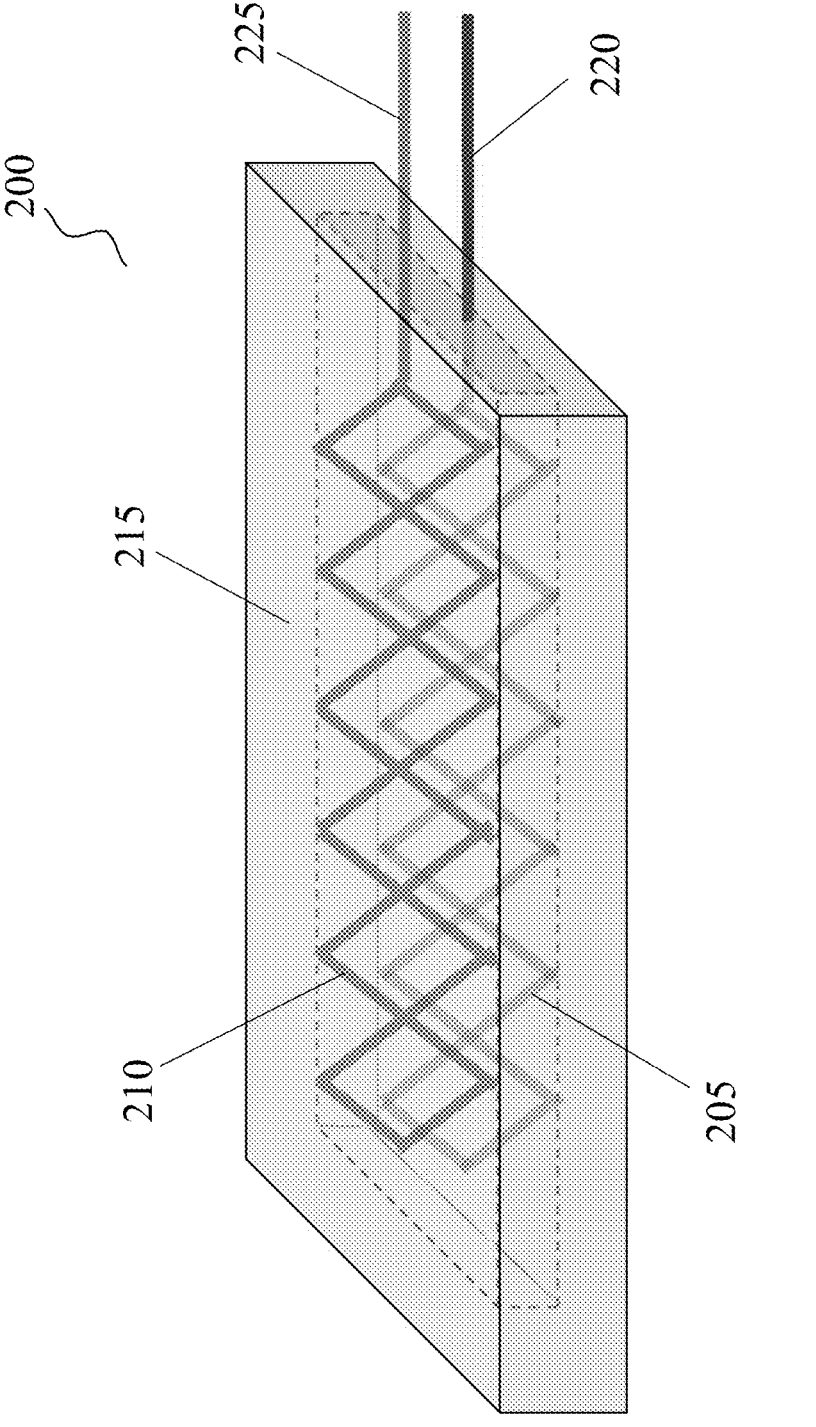
FIG. 2 depicts an exemplary plate electrode sensor according to an aspect of the present invention.

Now referring to FIG. 2, shown is an exemplary sensor 200 comprising a thin slab/membrane or plate electrode sensor geometry where the electrode meshes are laid out on the opposite sides of a thin nanoporous slab/membrane matrix. Electrode mesh 205 extends a lateral distance through nanoporous slab/membrane matrix 215. Electrode mesh 210 extends a lateral distance through nanoporous slab/membrane matrix 215 and is parallel to electrode mesh 205. The sensor's ends may be coated with an insulating coating to further prevent current leakage outside of the sensor. The nanoporous matrix 215 is depicted as the region surrounding the electrodes. The sensor's matrix is extended beyond the mesh electrode to provide protection. Electrical lead 220 extends outside of nanoporous slab/membrane matrix 215 and is in contact with electrode mesh 205. Electrical lead 225 extends outside of nanoporous slab/membrane matrix 215 and is in contact with electrode 210.

Sensor Systems

As contemplated herein, any version or type of sensor described herein may be incorporated into an additional housing or packaging system for placement within a concrete sample or structure.

Figure 3:
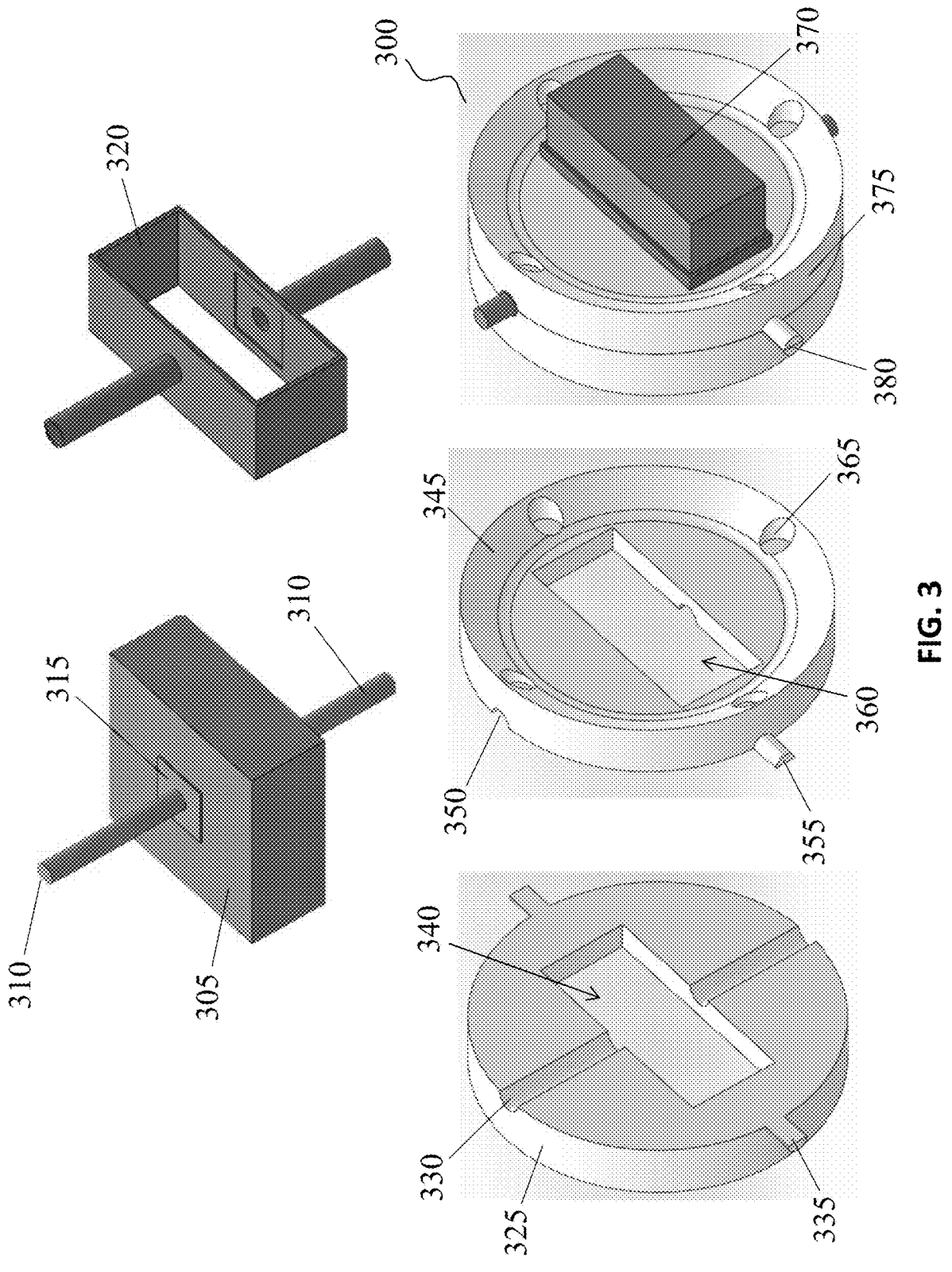
FIG. 3 depicts an exemplary cuboidal shape sensor and twist plug mounting package according to an aspect of the present invention.

Now referring to FIG. 3, shown is an exemplary, complete cuboidal sensor system 300 comprising a cuboidal pore solution resistivity sensor in a twist plug. Shown is cuboidal sensor matrix 305 with leads 310 connected to electrodes 315 in contact with sensor matrix 305 in diametrically opposed positions. Sensor matrix 305, leads 310, and electrodes 315 are encapsulated in encapsulating enclosure 320. Sensor matrix 305, leads 310, and electrodes 315 when encapsulated in encapsulating enclosure 320 forms cuboidal sensor system 370 to be enclosed inside cuboidal placement mechanism 375. Cuboidal placement mechanism 375 comprises bottom face 325 and top face 345 by which cuboidal sensor system 370 is secured when the two faces are adjoined. Cuboidal placement mechanism bottom face 325 comprises bottom lead channel 330, bottom frame mounting tab 335, and bottom sensor opening 340. Cuboidal placement mechanism top face 345 comprises top lead channel 350, top frame mounting tab 355, top sensor opening 360, and aperture 365. Aperture 365 on top face 345 is used to twist the placement mechanism 375 into a locked position once inserted into a holding frame. The complete sensor system 300 comprises sensor system 370 disposed between the top and bottom face of cuboidal placement mechanism 375. When bottom face 325 and top face 345 are adjoined, bottom frame mounting tab 335 and top frame mounting tab 355 align to form frame mounting tab 380. Although represented above as a circular object, it is to be noted that cuboidal placement mechanism 375 is not limited in shape or structure.

Figure 4:
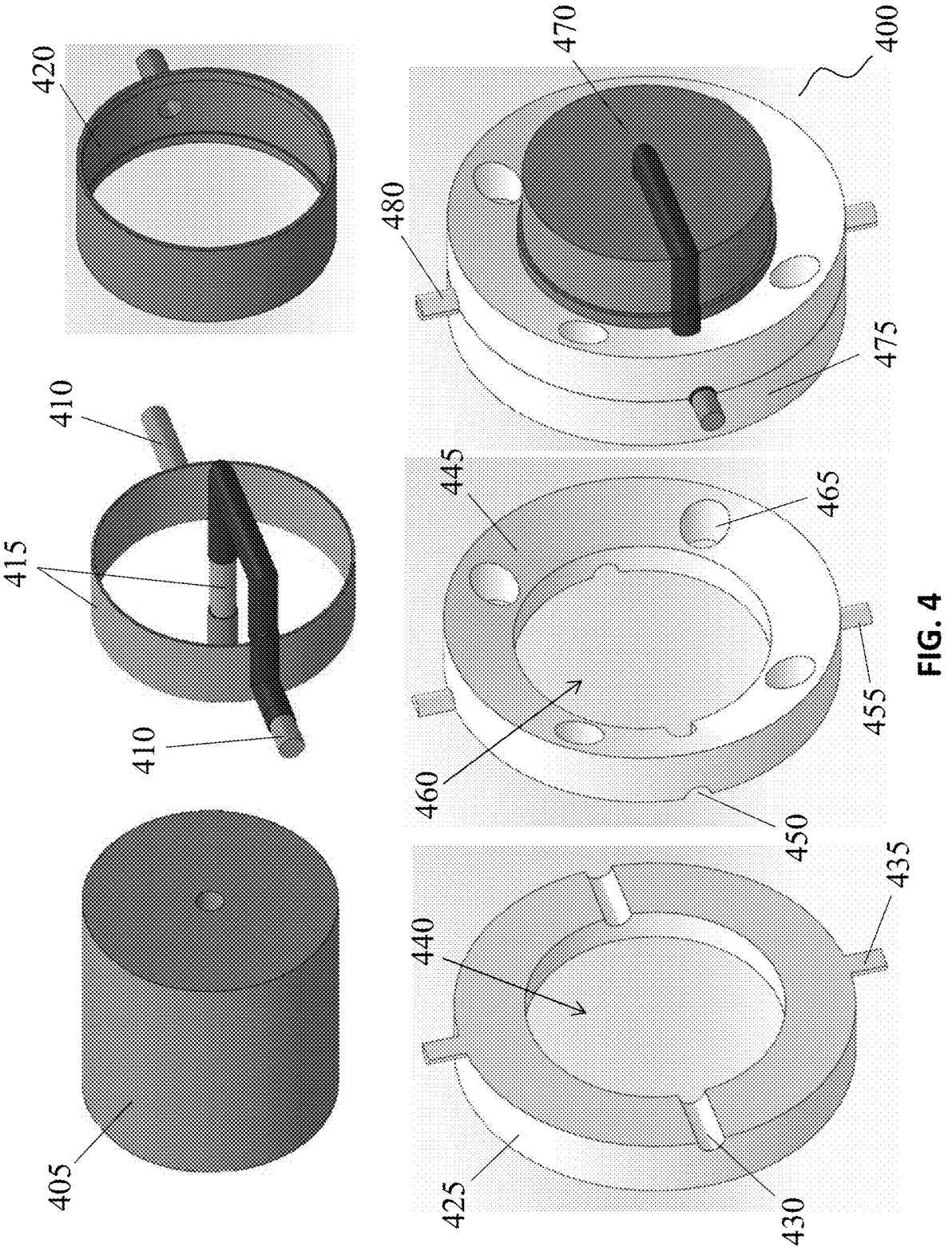
FIG. 4 depicts an exemplary cylindrical shape sensor and twist plug mounting package according to an aspect of the present invention.

Now referring to FIG. 4, shown is an exemplary, complete cylindrical/coaxial sensor system 400 comprising a cylindrical/coaxial pore solution resistivity sensor in a twist plug. Shown is cylindrical/coaxal sensor matrix 405 with leads 410 connected to electrodes 415 in contact with sensor matrix 405 in circumferential positions. Sensor matrix 405, leads 410, and electrodes 415 are encapsulated in encapsulating enclosure 420. Sensor matrix 405, leads 410, and electrodes 415 when encapsulated in encapsulating enclosure 420 form cylindrical/coaxial sensor system 470 to be enclosed inside cylindrical placement mechanism 475. Cylindrical placement mechanism 475 comprises bottom face 425 and top face 445 by which cylindrical/coaxial sensor system 470 is secured when the two faces are adjoined. Cylindrical placement mechanism bottom face 425 comprises bottom lead channel 430, bottom frame mounting tab 435, and bottom sensor opening 440. Cylindrical placement mechanism top face 445 comprises a top lead channel 450, top frame mounting tab 455, top sensor opening 460, and aperture 465. Aperture 465 on top face 445 is used to twist placement mechanism 475 into a locked position once inserted into a holding frame. The complete cylindrical/coaxial sensor system 400 comprises cylindrical/coaxial sensor system 470 disposed between the top and bottom face of cylindrical placement mechanism 475. When bottom face 425 and top face 445 are adjoined, bottom frame mounting tab 435 and top frame mounting tab 455 align to form frame mounting tab 480. Although represented above as a circular object, it is to be noted that cuboidal placement mechanism 475 is not limited in shape or structure.

Figure 5:
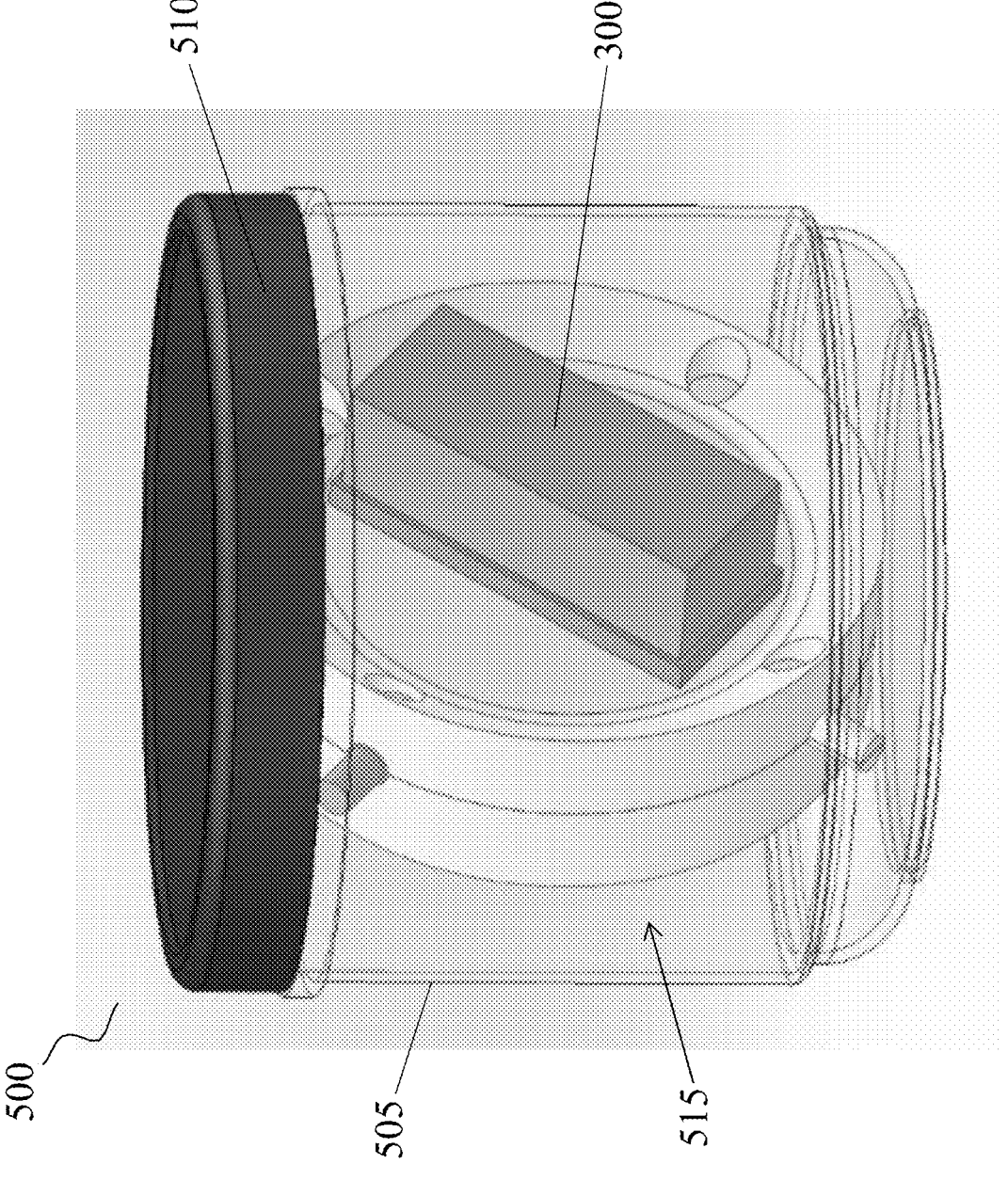
FIG. 5 depicts an exemplary cuboidal shape sensor inside a shipping container filled with simulated pore solution according to an aspect of the present invention.

Now referring to FIG. 5, a design of an exemplary shipping container filled with simulated pore solution is shown, to ensure full saturation of the pore solution resistivity sensor before placement in concrete. Shown in FIG. 5 is shipping container system 500, comprising container 505 with interior volume, container lid 510, simulated pore solution 515, with complete sensor system 300 disposed inside the interior volume of container 505.

Figure 6:
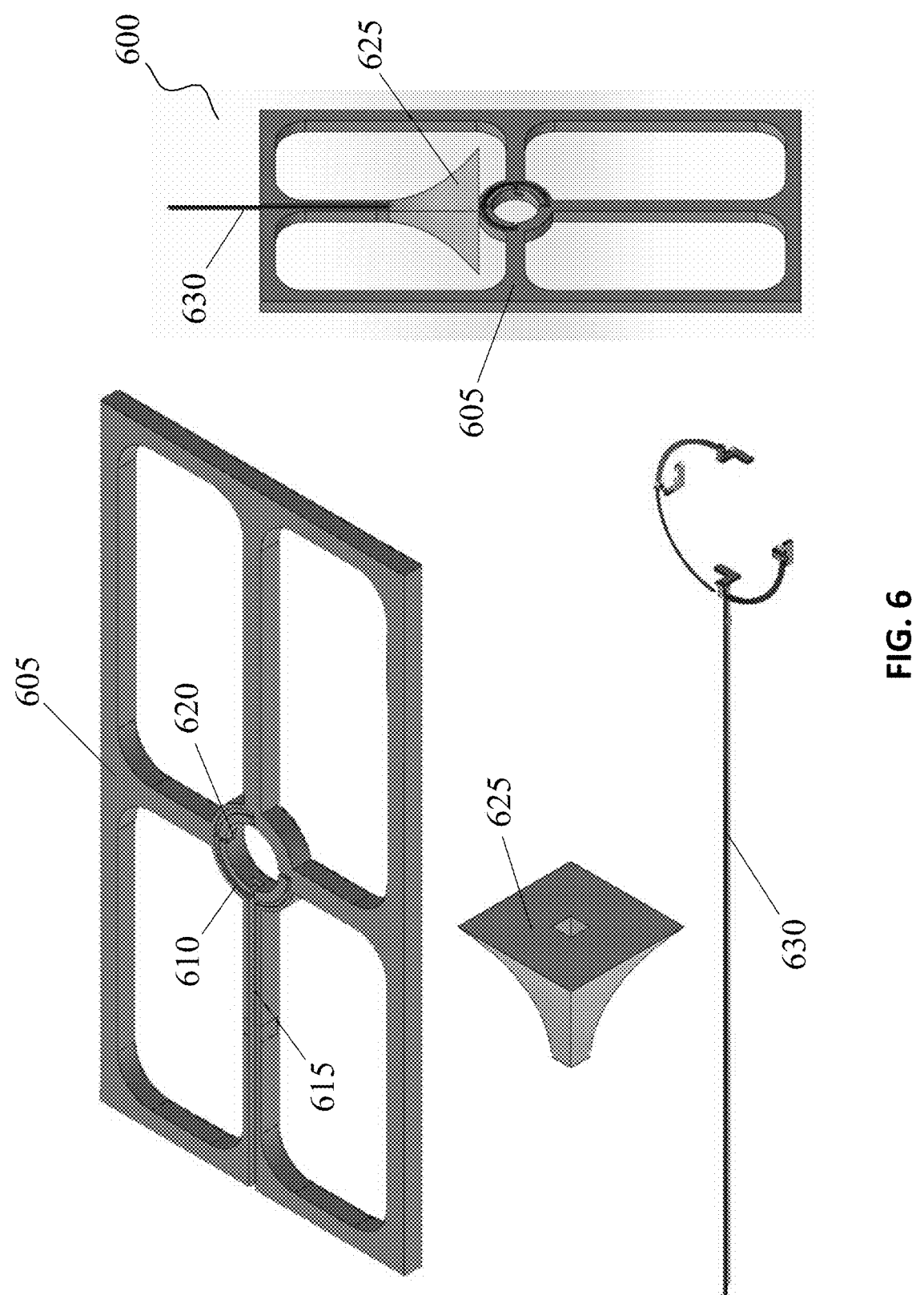
FIG. 6 depicts an exemplary holding frame to affix the sensor and twist plug mounting package according to an aspect of the present invention.

Now referring to FIG. 6, a design of an exemplary sensor-holding frame for placement of a pore solution resistivity sensor in cylindrical concrete samples. Shown in FIG. 6 is the frame system 600 comprising holding frame 605, sensor mounting location 610, lead wire guide channel 615, slotted recess 620, lead wire 630, and protective dome 625. It is to be noted that system 600 may mount either system 300 or system 400 at sensor mounting location 610 of holding frame 605. Frame mounting tabs 380 of complete cuboidal sensor system 300, and frame mounting tabs 480 of complete cylindrical/coaxial sensor system 400 interlock with slotted recess 620 located on holding frame 605 of frame system 600. The "twist plug" style system affixes sensor systems 300 or 400 through a push and twist locking style to holding frame 605 to construct system 600.

Figure 7:
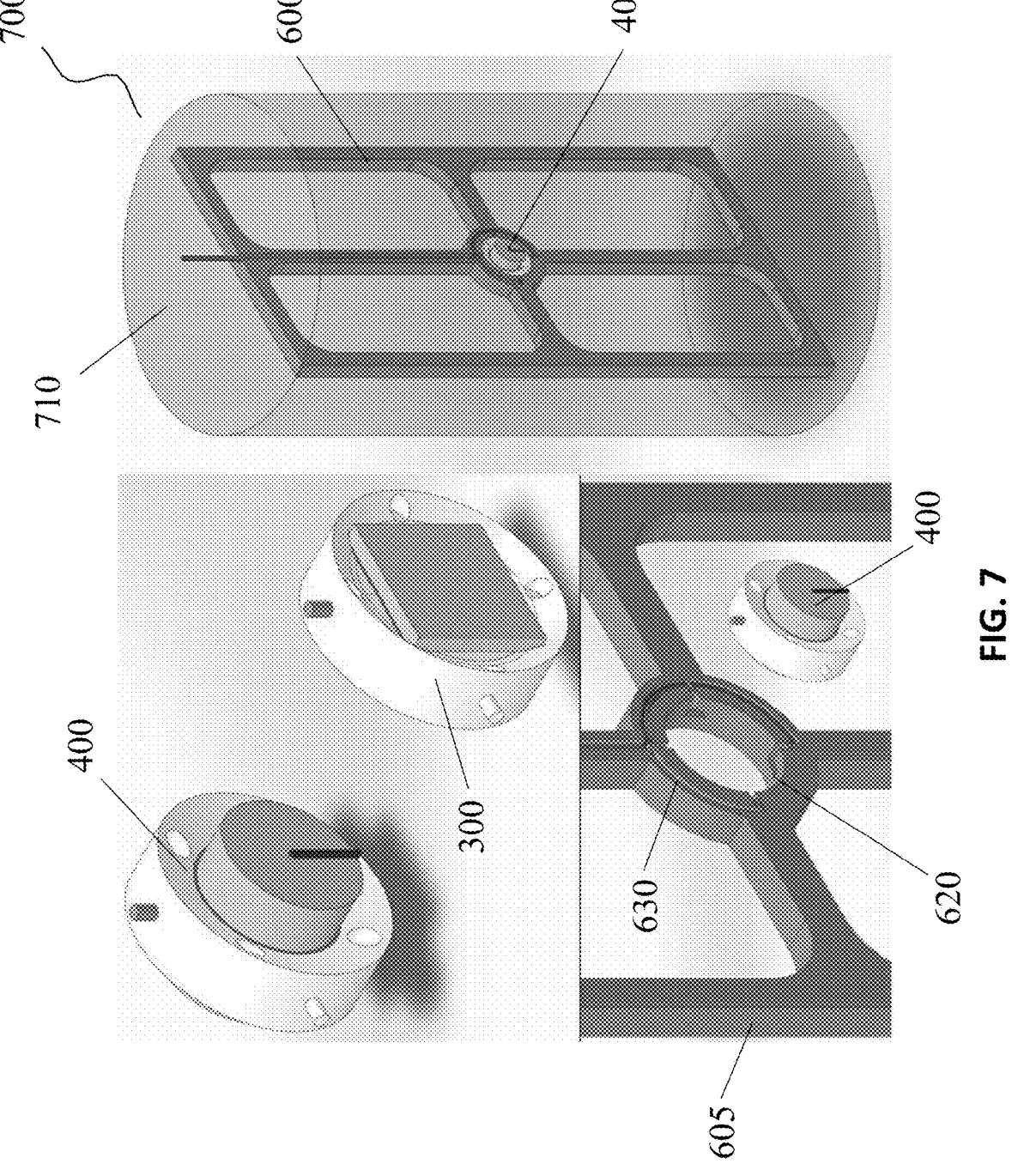
FIG. 7 depicts an exemplary holding frame with cylindrical shape sensor and twist plug mounting package embedded in a cylindrical concrete sample according to an aspect of the present invention.

Now referring to FIG. 7, an exemplary embodiment of a cylindrical concrete sample with the sensor holding frame with sensor system embedded within the interior volume of the concrete sample. Shown in FIG. 7 is cylindrical concrete system 700, comprising cylindrical concrete sample 710, frame system 600, and sensor system 400. It is to be noted that system 300, or system 400 will interlock with holding frame 605 of system 600, therefor the parts are considered interchangeable in system 600 and cylindrical concrete system 700.

In some embodiments, the size of holding frame 605 corresponds to the size of standard cylindrical concrete molds. For example, in one embodiment, the frame has a diameter of about 90-100 mm (3.5-4") and a height of about 170-190 mm (6.7-7.5"). In one embodiment, the frame has a diameter of about 140-150 mm (5.5-6") and a height of about 270-290 mm (10.5-11.4").

In some embodiments, the frame is shorter than the height of the concrete cylinder to allow free space for rolled lead wire to be stored under a molded cap. The frame must be 10-30 mm shorter than the cylinder height.

In some embodiments, cuboidal sensor matrix 305 of cuboidal sensor system 300 has a length, width and thickness to allow for the measurement of pore solution resistivity of concrete. The cuboidal sensor matrix dimensions must not exceed the following values: a length of 15 mm, a width of 15 mm, and a thickness of 6 mm.

In some embodiments, cylindrical sensor matrix 405 of cylindrical sensor system 400 has a diameter and height to allow for the measurement of pore solution resistivity of concrete. The cylindrical sensor matrix dimensions must not exceed the following values: a diameter of 15 mm and a height of 15 mm.

Sensor Components

Electrodes Terminals

In one embodiment, the first electrode is a current electrode. In one embodiment, the second electrode is a current electrode. In one embodiment, the sensor further comprises a first voltage and a second voltage electrode. In one embodiment, the sensor further comprises means for sensing the potential across said voltage electrodes. In one embodiment, the four electrode open-cell conductivity sensor includes two electrode pairs mounted in opposition.

In one embodiment, the two electrodes have a coaxial configuration. In one embodiment, the first electrode is a central cylindrical electrode having a smooth continuous surface for contact with the nanoporous sensor matrix. In one embodiment, the second electrode is an outer electrode surrounding the nanoporous sensor matrix, the outer electrode having a smooth continuous contact surface with the matrix. In one embodiment, the second electrode forms a mesh surrounding the matrix to allow physical contact between the matrix and the surrounding concrete. In one embodiment, the sensor comprises nanoporous matrix between the inner electrode and the outer electrode. In one embodiment, the central cylindrical electrode and the outer electrode form a continuous smooth plane surface for contact with the nanoporous matrix In some embodiments, the inner electrode has a cylindrical shape with a curved surface along its vertical extent that faces the outer electrode. In horizontal cross section, the inner electrode may have any curved profile ranging from a circle to an ellipse, for example, that is uniform along the vertical extent of the inner electrode. In other embodiments, the horizontal cross section of the cylindrical shaped inner electrode is non-uniform along its vertical extent. In some embodiments, the inner electrode has a cylindrical shape with planar surfaces along its vertical extent that faces the outer electrode. Some portions of the inner electrode will increase and then decrease along its vertical extent. Moreover, the inner electrode may be either solid or have a hollow center.

In some embodiments, the outer electrode is a cylinder with a curved outer surface along its vertical extent. In horizontal cross section, the outer electrode may be any curved profile ranging from a circle to an ellipse, for example. In other embodiments, the outer electrode is a hollow cylinder with planar outer surfaces along its vertical extent. In horizontal cross section, the outside profile of the outer electrode is a polygon, while the inside profile of is curved or planar, depending on the embodiment. The inside vertical surface of the outer electrode that faces the inner electrode may have a variety of contours from planar to curved.

In one embodiment, the electrodes are made of an electrically conductive material such as copper, stainless steel, or another metallic material. In certain embodiments, the electrodes are made of a homogeneous conductive metal. In certain embodiments, the electrodes are made of a non-single crystalline structure. In one embodiment, the inner electrode comprises a material with a non-single crystalline structure at its vertical surface. In one embodiment, the outer electrode comprises a material with either a non-single crystalline structure or a single-crystalline structure at its vertical surface that faces the inner electrode. A 'non-single crystalline' structure is defined herein to include within its scope a microcrystalline structure, a polycrystalline structure and an amorphous structure.

In some embodiments, the inner electrode comprises a non-single crystalline material at its vertical surface. In some embodiments, the outer electrode also comprises a non-single crystalline material on the inside vertical surface facing the inner electrode. In some embodiments, the non-single crystalline material is deposited on the surface of the respective electrodes. In other embodiments, one or both of the electrodes are formed of non-single crystalline materials, such that an additional non-single crystalline film is not included. The non-single crystalline materials may be the same or different on the electrodes. In one embodiment, the non-single crystalline material is highly electrically conductive or is rendered highly electrically conductive through doping.

In some embodiments, the non-single crystalline material includes, but is not limited to, a semiconductor, a metal and a metal alloy. In some embodiments, the non-single crystalline material is provided on a base material of the respective electrode as a thin film. In some embodiments, the base material itself of the respective electrodes is the non-single crystalline material. In some embodiments, the non-single crystalline material used herein is a semiconductor material, for example, polycrystalline silicon. In some embodiments, one or both of a metal material and metal alloy material may be used as a non-single crystalline material, for example. In some embodiments, the non-single crystalline material is one of a silicide, a carbide and a nitride of the metal or metal alloy.

The non-single crystalline semiconductor materials include, but are not limited to, Group IV semiconductors, compound semiconductors from Group III-V and compound semiconductors from Group II-VI having a non-single crystalline structure, as defined herein. For example, one or both of the inner electrode and the outer electrode may comprise a polycrystalline or a microcrystalline silicon (Si) or a non-single crystalline silicon germanium (SiGe) compound semiconductor. In another example, one or both of the electrodes may comprise gallium arsenide (GaAs) in a microcrystalline film. In another example, the inner electrode may comprise a hydrogenated silicon (Si:H) microcrystalline film while the outer electrode is an optically transparent material.

In one embodiment, the non-single crystalline semiconductor materials comprise tantalum nitride (TaN). The metals and metal alloys have inherent non-insulative character (i.e., an inherent non-insulator or inherently electrically conductive) for an electrode material. In some embodiments, the electrodes may be formed from metal foil layers, for example, a metal foil of non-single crystalline tantalum nitride (TaN) or a single crystalline TaN that further has a polycrystalline silicon film coating on the surface of the TaN electrodes.

In some embodiments, the exterior surface of the outer electrode is cylindrical and the overlap region is an elongated cylindrical shape, such that the flexible electrical device is a coaxial electrode.

In some embodiments the first electrode and the second electrode have a plate configuration, with the first electrode having a rectangular shape and the second electrode having a rectangular shape and lying in plane parallel with that of the first electrode, with a nanoporous matrix therebetween. In one embodiment, the electrodes may have any configuration known to those of skill in the art. In one embodiment, the electrodes may comprise any conductive material known to the art, including but not limited to metals and metal alloys, chalcogenides, graphite, graphene, carbon nanotubes and the like, and conductive 2D materials. In one embodiment, the electrodes may be in a mesh form to allow physical contact between the nanoporous matrix and the surrounding concrete.

In some embodiments, the first electrode and the second electrode are designed to as to support an influx of AC or DC current. In some embodiments, the first electrode and the second electrode are designed so as to prevent current leakage. In some embodiments, when a current is applied between the first electrode and the second electrode, a resistance is measured. In some embodiments, when a voltage is applied between the first electrode and the second electrode, a resistance is measured. In some embodiments, the resistance is used to calculate the electrical resistivity or conductivity of the pore solution.

Nanoporous Material (Matrix)

In one embodiment, the material or nanoporous matrix has a first surface directed toward the first electrode and a second surface directed toward the second electrode. In one embodiment, nanoporous matrix completely fills the space between the first electrode and the second electrode. In one embodiment, the first surface of the nanoporous matrix extends beyond the surface of the first electrode. In one embodiment, the second surface of the nanoporous matrix extends beyond surface of the second electrode.

In one embodiment, the nanoporous matrix comprises open pore, crosslinked ceramics, polymers, cementitious materials, or any other materials having a porous structure. In one embodiment, the pores of the nanoporous matrix have a mean width (diameter) of up to about 50 nm. In one embodiment, the mean width of the pores is up to about 45 nm. In one embodiment, the mean width of the pores is up to about 40 nm. In one embodiment, the mean width of the pores is up to about 35 nm. In one embodiment, the mean width of the pores is up to about 30 nm. In one embodiment, the mean width of the pores is up to about 25 nm. In one embodiment, the mean width of the pores is up to about 20 nm. In one embodiment, the mean width of the pores is up to about 15 nm. In one embodiment, the mean width of the pores is up to about 10 nm. In some embodiments, pores having a mean width greater than 50 nm are also contemplated. In one embodiment, the pores of the nanoporous matrix permit an equilibrium between the pore solution within the sensor and the pore solution outside the sensor.

In some embodiments, the nanoporous matrix comprises a nanoporous cementitious material. In some embodiments, the nanoporous cementitious material comprises a mature cement paste. This includes cement pastes with water to cementitious materials mass ratio w/cm<0.42 that are cured to maximum degree of hydration according to TC Power's model (S. Mindess, J. F. Young, D. Darwin, (2003). Concrete, 2nd Ed., Prentice Hall) until the capillary pore space has been filled up with hydration products.

In some embodiments, the nanoporous cementitious material also comprises a high quality SCM such as silica fume or metakaolin to consume the soluble portlandite $(Ca(OH)_2)$ and further stabilize the sensor's pore structure.

In one embodiment, the nanoporous cementitious material is cured via steam curing at 50° C. or autoclave curing at 180° C. and steam pressures of up to 20 atm to produce a nanoporous tobermorite skeleton with high stability. In some embodiments, the nanoporous cementitious material comprises a geopolymer where an alumino-silicate precursor material (including but not limited to metakaolin, calcined clay, natural pozzolan, volcanic ash, fly ash, ground bottom ash, or slag cement) is chemically activated in exposure to water and alkaline chemicals. Examples of alkaline chemicals include but are not limited to alkali hydroxides, alkali silicates, alkali carbonates, alkali sulfates, alkali sulfites, alkali lactates, calcium hydroxide, and magnesium hydroxide.

In some embodiments, the geopolymer is cured at room temperature (e.g., 23° C.). In other embodiments, the geopolymer is cured at higher temperatures (e.g., 60° C.).

In some embodiments, the nanoporous matrix is electrically insulative/non-conductive. In some embodiments, the nanoporous matrix is resistant to harsh aqueous conditions, such as but not limited to, high pH conditions (pH≥13), low pH conditions (pH≤1), and oxidizing/reducing conditions (such as electrical currents).

In one embodiment, the nanoporous matrix comprises an outer shell covering the entirety of the nanoporous matrix, said shell having pores of mean width greater than or equal to that of the nanoporous matrix. In one embodiment, the outer shell is electrically insulative/non-conductive. In one embodiment, the electrically insulating outer shell permits the use of a wider variety of materials in the nanoporous matrix, such as materials which are poorer electrical insulators. In one embodiment, the outer shell comprises a material which is deposited over the nanoporous matrix. In one embodiment, the outer shell and the nanoporous matrix are connected via covalent bonds. In one embodiment the outer shell comprises small molecules, ceramics, or polymers which are covalently bound to the outer surface of the nanoporous matrix. In some embodiments, the outer shell of the nanoporous matrix 1 is resistant to harsh aqueous conditions, such as but not limited to, high pH conditions (pH≥13), low pH conditions (pH≤1), and oxidizing/reducing conditions (such as electrical currents).

In one embodiment, the nanoporous matrix comprises halloysite nanotubes. Halloysite nanotubes (HNTs) are a kind of silicate inorganic material with natural nanotube structure, having excellent thermal and mechanical properties, and have applications in the field of reinforced or toughened polymer material, carriers for orientation drug release, etc. In one embodiment, HNTs comprise modified halloysite nanotubes (m-HNTs). HNTs are hydrophilic, and m-HNTs are hydrophobic due to grafting aliphatic chain on the surface of HNTs. In one embodiment, polymers are used as dispersion medium in the present invention, and some polymers are hydrophobic. Following similar dissolve mutually theory, the m-HNTs are dispersed well in hydrophobic polymers, thereby well dispersion of HNTs with high concentration in hydrophobic polymers could be ensured, leading to uniform pore diameter of the prepared inorganic material without obvious defects of microstructure. In one embodiment, the polymers may be one or two or more selected from plystyrene (PS), polyacrylonitrile (PAN), polyvinylpyrrolidone (PVP), polyl(actic-co-glycolic acid) (PLGA), polyving akohol (PVA), polyethylene oxide (PEO), polyamide (PA). In one embodiment, the number average molar weight of the polymer is between $10^5$ to $1.5 \times 10^6$.

In one embodiment, the nanoporous matrix comprises a nanoporous ceramic material. In one embodiment, the nanoporous ceramic material is produced from ceramic precursor materials known to those of skill in the art. Ceramic precursor materials which are preferred for the purposes of this invention include oligomers and polymers such as polysilazanes, polycarbosilazanes, polycarbosilanes, vinylic polysilanes, amine boranes, polyphenylborazanes, carboranesiloxanes, polysilastyrene, polytitanocarbosilanes and like materials, as well as mixtures thereof, whose pyrolysis products yield ceramic compositions containing structural units having bond linkages selected from Si—C, Si—N, Si—C—N, Si—B, Si—B—N, Si—B—C, Si—C—N—B, B—N and B—N—C, as well as oxycarbide and oxynitride bond linkages such as Si—O—N and Ti—O—C. The preferred precursors are those oligomers and polymers having a number average molecular weight in the range of from about 200 to about 100,000 g/mole, more preferably from about 400 to about 20,000 g/mole. The chemistry of these oligomeric and polymeric precursors is further disclosed in the monograph "Inorganic Polymers", J. E. Mark, H. R. Allcock, and R. West, Prentice Hall, 1992.

In one embodiment, the polysilazanes contain, for example, recurring —Si(H)(CH₃)—NH— and —Si(CH₃)₂—NH— units and are prepared by reacting one or a mixture of monomers having the formula $R_1SiHX_2$ and $R_2R_3SiX_2$ in anhydrous solvent with ammonia. In the above formulas, $R_1$, $R_2$ and $R_3$ may be the same or different groups selected from hydrocarbyl, alkyl silyl or alkylamino and $X_2$ is halogen. The preferred polysilazanes are prepared using methyldichlorosilane or a mixture of methyldichlorosilane and dimethyldichlorosilane as monomer reactants with ammonia. The primary high temperature pyrolysis products (>1300° C.) of this precursor are silicon nitride ($Si_3N_4$) and silicon carbide (SiC). In one embodiment, these precursors are have a number average molecular weight of about 6300 and 1300 respectively.

In one embodiment, the polysilazane precursors are poly-organo (hydro) silazanes having units of the structure $(RSiHNH)_x(R_1SiH)_{1.5}N_{1-x}$ where $R_1$ is the same or different hydrocarbyl, alkylsilyl, alkylamino or alkoxy and $0.4<X<1$. These materials are disclosed in U.S. Pat. No. 4,659,850, the complete disclosure of which is incorporated herein by reference.

In one embodiment, the ceramic precursor is a polysilas-tyrene having the structure—(phenyl)(methyl) Si—Si (methyl)$_{2-n}$. In one embodiment, this material has a number average molecular weight of about 2000 and the primary pyrolysis products of this precursor in an inert atmosphere are silicon carbide and carbon.

In one embodiment, the ceramic precursors are polycar-bosilanes having units of the structure $(Si(CH_3)_2CH_2)_n$ and/or $(SiH(CH_3)CH_2)_n$ having a number average molecular weight in the range of about 1000 to 7000. In one embodi-ment, the main pyrolysis product of these materials (>1300° C.) in an inert atmosphere are silicon carbide and excess carbon.

Other suitable preceramic precursors will be evident to those skilled in the art, particularly those yielding SiC, $Si_3N_4$, Si—C—N, BN, Si—B—N, B+C—BN—C and Si—B—C as pyrolysis products.

In one embodiment, the ceramic precursor may also contain one or a mixture of particulate materials which promote the formation of micro- and nano-porosity in the ceramic during pyrolysis, particularly when pyrolysis is conducted in the presence of flowing inert gas such as helium, argon or nitrogen. For example, the precursor may also be mixed with up to 50 wt % of ceramic particles such as silicon carbide, silicon nitride, silicon-carbide-nitride and mixtures thereof having a mean particle size of less than about 10 microns. Other particles which may be mixed with ceramic precursor include non-silicon containing particles also having a mean particle size of less than 10 microns, such as carbon, alumina, aluminosilicates or nitrides or carbides of metals such as aluminum, boron, molybdenum, manganese, titanium, zirconium or tungsten and mixtures thereof, present at a level of up to about 60 wt %. Other particles which promote the development of a nanoporous structure include solid metal particles having a mean particle size of from about 1 to about 10 nm present in the prece-ramic intermediate at a level of up to 35 wt %.

In one embodiment, pyrolysis of the ceramic precursor is conducted by heating it under flowing gas, e.g., argon, helium or nitrogen, or under flowing ammonia gas, at a controlled rate of temperature, with preferred hold times at intermediate temperatures to maintain uniformity of the ceramic product, and a final hold time at the maximum heating temperature, followed by gradual cooling of the ceramic end product to room temperature. In one embodi-ment, microporous ceramics are formed by gradually heat-ing the precursor or precursors to a maximum temperature $(T_{max})$, in the range of from about 300° C. to less than about 1100° C. at a heating rate in the range of from about 1° C. to 10° C. per minute, with various holding times of about 0.5 to about 5 hours at selected temperatures between about 200° C. and $T_{max}$. Total combined heating/holding times may range from about 3 to about 50 hours, more preferably from about 5 to about 24 hours. In one embodiment, holding times and temperatures are dictated by ceramic precursor decomposition and reaction kinetics. In one embodiment, they depend on precursor composition and the rate of evolution of specific molecular species at or about the holding temperature, e.g., $H_2$, $CH_4$, higher molecular weight hydrocarbon or H—C—N species, or ceramic precursor fragments as reflected by sample weight losses at or about these temperatures. In one embodiment, the flow rate of the inert gas or ammonia gas may range from about 100 to about 1000 cc/min.

In one embodiment, the pyrolysis may be carried out by continuous heating of the ceramic precursor up to $(T_{max})$ or by sequential heating including hold times at intermediate temperatures below $(T_{max})$. As a general rule where the heating rate is slow, e.g., less than about 5° C./min. or 300° C. per hour, intermediate holding times below $(T_{max})$ may not be necessary in order to form the desired microporous structure. Where the heating rate is more intense, e.g., 5° C./min. or 300° C. per hour or higher, then holding times at one or more intermediate temperatures below $(T_{max})$ will generally be necessary to achieve the desired microporous structure.

In one embodiment, the nanoporous matrix comprises a selective sol-gel ceramic material, said sol-gel ceramic material comprising a porous support having a plurality of support pores that are 50 nm or greater in diameter and a nanoporous composite comprising a nanoporous sol-gel ceramic composite filling at least a portion of the porous support; wherein the nanoporous composite comprises a plurality of nanopores of about 10 nm or smaller in radius with a polydispersity index of about 0.5 or lower. In one embodiment, the nanoporous selective sol-gel ceramic mate-rials can be formed without high-temperature processing of the ceramic. In one embodiment, the structure is accom-plished, for example, by lining the edge of a porous support with a compressible polymer and filling in the porous support with a sol-gel ceramic composite. In one embodi-ment, this approach enables the active area to be mechani-cally decoupled from the compression region, thus provid-ing a route to use non-sintered and non-calcinated sol-gel ceramic containing materials in filtration and separation processes.

In one embodiment, the selective sol-gel ceramic material comprises three components that serve distinct purposes: a macroporous support, a nanoporous composite layer, and a polymeric edge. In one embodiment, the macroporous sup-port structure is capable of wetting a solvent based ceramic dispersion/solution (e.g., siloxane) in order to create a nan-oporous (i.e., <50 nm) ceramic structure. In one embodi-ment, the nanoporous composite layer is within the mac-roporous support structure with characteristic porosity of <10 nm. In one embodiment, the compressible polymer edge, when present, eliminates or reduces compressive forces on the nanoporous sol-gel selective ceramic layer while enabling liquid-tight sealing at the edges. In certain circumstances, the porous support structures can also con-tain a pre-coating (i.e., prior to the nanoporous sol-gel) to improve mechanical, chemical or electro-chemical stability. In other circumstances, materials can undergo a post treat-ment chemical bath to further induce gelation.

In one embodiment, the porous material support, or the ceramic nanoporous material, (sometimes referred to herein simply as the "porous support" or "support") is the structural foundation within and/or upon which the nanoporous selec-tive sol-gel ceramic is formed. In one embodiment, the support provides mechanical strength and a porous structure. Typically, the porous substrates comprise support pores with an average support pore radius between about 10 nm and about 50 μm. In some embodiments, the support pores have an average radius of about 10 nm or greater. In one embodiment, when the ceramic is formed on the support, the relatively large pores of the support are closed and filled with the ceramic until nanometer- or angstrom-sized pores remain in the final nanoporous ceramic material.

Any suitable organic or inorganic material can be used as a porous support or as a ceramic nanoporous material. In some embodiments, the porous support comprises a material selected from the group consisting of a polymeric material, a ceramic material, a nonconductive metal, and a combination thereof. In one embodiment, the porous substrate can comprise a nonwoven fabric, a nonwoven mesh, a veil, a knit fabric, a woven fabric, a woven mesh, an open-cell foam, and combinations thereof. In some embodiments, the porous support has a chemical surface functionality that is chemically similar to the ceramic precursor sol used to form the material; for example, a silica mesh can be used as a support for forming a silica-based sol-gel ceramic material of the disclosure. In other embodiments, the porous support is chemically different from the ceramic precursor sol used to form the material. For instance, a silica sol can be used to form an exemplary material by filling at least a portion of a polymeric or metal membrane.

In some embodiments, the porous support comprises a material selected from the group consisting of polypropylene, polyethylene, polyvinyl chloride, polystyrene, polyamide, polyimide, polyacetonitrile, polyvinylacetate, polyethylene glycol, poly ether ketone, polysulfone, polysulfonamide, polyacrylamide, polydimethylsiloxane, polyvinylidene fluoride, polyacrylic acid, polyvinyl alcohol, polyphenylene sulfide, polytetrafluoroethylene, cellulose, and combinations thereof. In one embodiment, the porous support is selected from the group consisting of silica filter paper, polyvinylidene fluoride (PVDF), polyether ether ketone (PEEK), and polytetrafluoroethylene (PTFE). In certain embodiments, the nanoporous ceramic material comprises silica, titania, germania, zirconia, alumina, graphite, silicon carbide, silicon nitride, boron nitride, borosilicate glass, lithium silicate, potassium silicate, tin oxide, iron oxide, carbon nanotubes, iron, or a combination thereof.

In some embodiments, the nanoporous selective sol-gel ceramic materials are prepared by coating the porous support with a sol-gel precursor composition comprising one or more ceramic precursors and gelling the sol-gel precursor composition to form nanoporous sol-gel ceramic composite within the porous support.

Suitable ceramic precursors include silica, siloxane, silicate ester, silanol, silane, ormosil, titania, zirconia, germania, alumina, graphite, silicon carbide, silicon nitride, boron nitride, and combinations thereof. In some embodiments, the ceramic precursor comprises tetraalkyl orthosilicates, silanols, silanes, halosilanes, and combinations thereof.

Typically, the ceramic precursors include small molecules (i.e., <2 nm radius) and generally account for about 20 volume % or more of a sol-gel precursor composition. In some embodiments, the ceramic precursors account for about 40 volume % or more of a sol-gel precursor composition. In some embodiments, the ceramic precursors account for about 60 volume % or more of a sol-gel precursor composition.

In some embodiments, the ceramic precursor comprises tetraalkyl orthosilicate of formula $Si(OR)+$, wherein R is an optionally substituted C1-C15 alkyl. In some embodiments, the tetraalkyl orthosilicate is tetraethyl orthosilicate (TEOS).

In some embodiments, the ceramic precursor comprises one or more organosilanes of the formula $R^*_2$—Si—$(OR)_2$ or $R^*$-Si—$(OR)_3$, wherein $R^*$, independently at each occurrence, is an optionally substituted C1-C15 alkyl, optionally substituted C4-C20 heteroalkyl, optionally substituted aryl, or optionally substituted heteroaryl, and R, independently at each occurrence, is an optionally substituted C1-C6 alkyl. In some embodiments, the organosilane is $C_6H_{13}$—Si—$(OR)_3$.

As used herein, the term "alkyl" includes straight-chain, branched-chain, and cyclic monovalent hydrocarbyl radicals, and combinations thereof, which contain only C and H when they are unsubstituted. The term "alkyl," as used herein, includes cycloalkyl and cycloalkylalkyl groups. Examples include methyl, ethyl, isobutyl, cyclohexyl, cyclopentylethyl, and the like. The total number of carbon atoms in each such group is sometimes described herein, e.g., when the group can contain up to ten carbon atoms, it can be represented as 1-10C, C1-C10, $C_1$-$C_{10}$, C1-10, or $C_{1-10}$. The term "heteroalkyl," as used herein, means the corresponding hydrocarbons wherein one or more chain carbon atoms have been replaced by a heteroatom. Exemplary heteroatoms include N, O, S, and P. When heteroatoms are allowed to replace carbon atoms, for example, in heteroalkyl groups, the numbers describing the group, though still written as e.g. C3-C10, represent the sum of the number of carbon atoms in the cycle or chain plus the number of such heteroatoms that are included as replacements for carbon atoms in the cycle or chain being described.

Alkyl groups can be optionally substituted to the extent that such substitution makes sense chemically. Typical substituents include, but are not limited to, halogens (F, Cl, Br, I), =O, =NCN, =NOR, =NR, OR, $NR_2$, SR, $SO_2R$, $SO_2NR_2$, $NRSO_2R$, $NRCONR_2$, NRC(O)OR, NRC(O)R, CN, C(O)OR, C(O)$NR_2$, OC(O)R, C(O)R, and $NO_2$, wherein each R is independently H, $C_1$-$C_8$ alkyl, $C_2$-$C_8$ heteroalkyl, $C_1$-$C_8$ acyl, $C_2$-$C_8$ heteroacyl, $C_2$-$C_8$ alkenyl, $C_2$-$C_8$ heteroalkenyl, $C_2$-$C_8$ alkynyl, $C_2$-$C_8$ heteroalkynyl, $C_6$-$C_{10}$ aryl, or $C_5$-$C_{10}$ heteroaryl, and each R is optionally substituted with halogens (F, Cl, Br, I), =O, =NCN, =NOR', =NR', OR', $NR'_2$, SR', $SO_2R'$, $SO_2NR'_2$, $NR'SO_2R'$, $NR'CONR'_2$, NR'C(O)OR', NR'C(O)R', CN, C(O)OR', C(O)$NR'_2$, OC(O)R', C(O)R', and $NO_2$, wherein each R' is independently H, $C_1$-$C_8$ alkyl, $C_2$-$C_8$ heteroalkyl, $C_1$-$C_8$ acyl, $C_2$-$C_8$ heteroacyl, $C_6$-$C_{10}$ aryl or $C_5$-$C_{10}$ heteroaryl. Alkyl groups can also be substituted by $C_1$-$C_8$ acyl, $C_2$-$C_8$ heteroacyl, $C_6$-$C_{10}$ aryl or $C_5$-$C_{10}$ heteroaryl, each of which can be substituted by the substituents that are appropriate for the particular group.

"Aromatic" or "aryl" substituent or moiety refers to a monocyclic or fused bicyclic moiety having the well-known characteristics of aromaticity; examples of aryls include phenyl and naphthyl. Similarly, "heteroaromatic" and "heteroaryl" refer to such monocyclic or fused bicyclic ring systems which contain as ring members one or more heteroatoms. Suitable heteroatoms include N, O, and S, inclusion of which permits aromaticity in 5-membered rings as well as 6-membered rings. Typical heteroaromatic systems include monocyclic $C_5$-$C_6$ aromatic groups such as pyridyl, pyrimidyl, pyrazinyl, thienyl, furanyl, pyrrolyl, pyrazolyl, thiazolyl, oxazolyl, and imidazolyl, and fused bicyclic moieties formed by fusing one of these monocyclic groups with a phenyl ring or with any of the heteroaromatic monocyclic groups to form a $C_8$-$C_{10}$ bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-14 ring member atoms. Typically, monocyclic heteroaryls contain 5-6 ring members, and bicyclic heteroaryls contain 8-10 ring members.

Aryl and heteroaryl moieties can be substituted with a variety of substituents including $C_1$-$C_8$ alkyl, $C_2$-$C_8$ alkenyl, $C_2$-$C_8$ alkynyl, $C_5$-$C_{12}$ aryl, $C_1$-$C_8$ acyl, and heteroforms of these, each of which can itself be further substituted; other substituents for aryl and heteroaryl moieties include halogens (F, Cl, Br, I), OR, $NR_2$, SR, $SO_2R$, $SO_2NR_2$, $NRSO_2R$, $NRCONR_2$, NRC(O)OR, NRC(O)R, CN, C(O)OR, C(O) $NR_2$, OC(O)R, C(O)R, and $NO_2$, wherein each R is independently H, $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_6$-$C_{10}$ aryl, $C_5$-$C_{10}$ heteroaryl, $C_7$-$C_{12}$ arylalkyl, or $C_6$-$C_{12}$ heteroarylalkyl, and each R is optionally substituted as described above for alkyl groups. The substituent groups on an aryl or heteroaryl group can be further substituted with the groups described herein as suitable for each type of such substituents or for each component of the substituent. Thus, for example, an arylalkyl substituent can be substituted on the aryl portion with substituents described herein as typical for aryl groups, and it can be further substituted on the alkyl portion with substituents described herein as typical or suitable for alkyl groups.

"Optionally substituted," as used herein, indicates that the particular group being described can have one or more hydrogen substituents replaced by a non-hydrogen substituent. In some optionally substituted groups or moieties, all hydrogen substituents are replaced by a non-hydrogen substituent (e.g., a polyfluorinated alkyl such as trifluoromethyl). If not otherwise specified, the total number of such substituents that can be present is equal to the number of H atoms present on the unsubstituted form of the group being described. Where an optional substituent is attached via a double bond, such as a carbonyl oxygen or oxo (=O), the group takes up two available valences, so the total number of substituents that may be included is reduced according to the number of available valences. As used herein, optional substituents include negatively charged groups, negatively chargeable groups, positively charged groups, positively chargeable groups, hydrophilic groups, and hydrophobic groups. In some embodiments, optional substituents include a group oxidizable to a sulfonic acid group, a thiol group (i.e., S—H), an alkylthiol group, sulfonic acid group, carboxylic acid group, amino group, and ammonium group.

In some embodiments, the ceramic precursors comprise groups, e.g., optional substituents, which functionalize the nanoporous ceramic material. For example, in some embodiments, the ceramic precursor comprises a silane with a sulfonic acid group to improve proton conductivity or molecular selectivity. Exemplary compounds include 3-trihydroxysilyl-1-propanesulfonic-acid and triethoxy(hexyl)silane. Other embodiments include a silane with a long alkane group to improve durability or reduce pore size. Exemplary silanes include triethoxy(hexyl)silane.

In some embodiments, the ceramic precursor comprises colloidal ceramic particles. Exemplary colloidal ceramic particles include colloidal silica particles, for example, Ludox® particles. In some embodiments, colloidal silica particles, e.g., Ludox® particles, are mixed with a bifunctional ($R^*_2$-Si—$(OR)_2$) or a trifunctional organosilane ($R^*$-Si—$(OR)_3$). Suitable colloidal particles include Ludox® SM-30, Ludox® HS-40, and Ludox® CL. The type of organosilane used in combination with the colloidal silica particles depends on the application. For example, organosilane comprising alkyl groups can be used to aid selectivity and organosilane comprising sulfonic groups can be used to aid proton conductivity.

Ceramic precursors comprising elements other than silicon (Si) can be used in the preparation of the nanoporous selective sol-gel ceramic materials disclosed herein. In some embodiments, the ceramic precursor comprises a titanium compound of the formula $Ti(OH)_x(OR)_y$, wherein R, independently at each occurrence, is an optionally substituted C1-$C_6$ alkyl, x is an integer ranging from 0 to 4, and x is an integer ranging from 0 to 4, and the sum of x and y is 4. In some embodiments, the ceramic precursor comprises titanium alkoxides, including tetraisopropoxide (TTIP) and/or its partially hydrolyzed species.

In certain embodiments, the ceramic precursor comprises an aluminum compound $Al(OR)_3$, wherein R, independently at each occurrence, is H or an optionally substituted C1-$C_6$ alkyl. Aluminum alkoxides, including aluminum isopropoxide (ATP), are some of the exemplary compounds suitable for use as ceramic precursors of the materials disclosed herein.

In some embodiments, the ceramic precursor comprises a germanium alkoxide. Suitable germanium alkoxides include, but are not limited to, mon-, di-, tri-, and tetraalkoxy germanane, such as, tetraethoxygermane, tetramethoxygermane, tetrapropoxygermane, and tetrabutoxygermane. The germania-based sol-gel precursor can also be hydrolyzed germanium alkoxide monomers, dimers, and/or trimers. In some embodiments, ceramic precursors comprise tetraalkyl orthogermanate Ge(OR)+. In some embodiments, ceramic precursors comprising mixtures of tetraethyl orthosilicate, $Si(OC_2H_5)_4$ and tetraethyl orthogermanate, $Ge(OC_2H_5)_4$ can be useful in preparation of the nanoporous materials disclosed herein.

In some embodiments, sol-gel precursor composition comprising multiple components described above can also be used as independent precursors or as composite precursors such as core-shell particles (e.g. alumina-coated silica nanoparticles). The precursor can be a pure material or a solution or dispersion in water and/or one or more other solvents. Further, the ceramic precursors can be applied as an emulsion or dispersion in water or other suitable solvents.

In certain embodiments, additives are added to a sol-gel precursor composition in order to enable specific desirable properties of the nanoporous selective sol-gel ceramic material when formed.

In some embodiments, the sol-gel precursor composition further comprises an additive selected from the group consisting of a selectivity additive configured to increase ion transport properties of the nanoporous selective sol-gel ceramic material, a durability additive configured to improve durability of the nanoporous selective sol-gel ceramic material, and a catalyst additive configured to add catalytic properties to the nanoporous selective sol-gel ceramic material. Suitable additives include catalyst, an ion-conducting polymer, electrically conductive particles, mechanical properties-improving materials, and a combination thereof.

In certain embodiments, the additive is a selectivity additive selected from the group consisting of an ionic-conducting polymer and a gas conducting polymer. To improve selectivity, in certain embodiments a polymer is an additive used to facilitate selective ion transport. For example, proton conducting polymers such as polystyrene sulfonate (PSS), polydiallyldimethylammonium chloride (PolyDADMAC), sulfonated nanocrystalline cellulose, sulfonated poly ether ether ketone (SPEEK), sulfonated polybenzimidazole (S-PBI) or perfluorosulfonic acid (PFSA). In other embodiments, the additive is a polymers (i.e., polyvinyl alcohol, polyacrylic acid, polyacrylamide, polyethylene glycol and others) promoting selective transport of other molecules (e.g., gases or other ions). Any additive polymers are soluble or dispersible in the sol-gel precursor composition. Furthermore, they must be able to handle the harsh environments or be protected from degradation by the oxide.

In some embodiments, the additive is a durability additive selected from the group consisting of a low Young's modulus polymer configured to provide increased flexibility to the ceramic selective material and a high Young's modulus polymer configured to provide increased durability to the nanoporous selective sol-gel ceramic material.

In certain embodiments, the durability additive is a polymer. A low Young's modulus polymer additive will lead to flexibility of the final material or a high Young's modulus will lead to improved durability of the final material. These are soluble or dispersible in the sol-gel precursor composition able to handle the harsh environments defined earlier or be protected from degradation by the oxide. Representative durability polymer additives include polyvinyl alcohol, polyacrylic acid, polyacrylamide, and polyethylene glycol, as well as combinations and copolymers thereof.

In one embodiment, the additive is a catalyst additive selected from the group consisting of catalytic particles added to the sol-gel precursor composition and catalytic particles formed within the sol-gel precursor composition. The catalyst additive is selected from the following schemes: (1) the addition of catalytic nano- or microparticles to the sol; (2) forming catalytic particles within the sol (e.g., prior to gelation/self-assembly); (3) forming catalytic particles during the sol-gel; and (4) applying/coating the surface of the active area with catalytic particles after it is cured. Platinum is an example a catalyst additive. In an embodiment, the catalyst additive is suitable to handle the harsh environments to which the material is exposed (if contained externally) or is protected from degradation by the ceramic material (if contained internally). In one embodiment, the catalyst additive is 10 vol % or less of the nanoporous selective sol-gel ceramic material.

The additives disclosed herein can be present in the final material in any suitable amounts, which are specific to the additive used. For example, for PSS & PDDA, it is typically advantageous to have a final loading (i.e., dry with water/solvent removed) of between about 3 wt % and about 40 wt %, between about 3 wt % and about 20 wt %, between about 3 wt % and about 10 wt %. In certain embodiments, the additive is present in an amount of 10 volume % or less of the sol-gel precursor composition.

In some embodiments, the sol-gel precursor composition further comprises one or more organic solvents. Any suitable organic solvent can be included in the sol-gel precursor. In some embodiments, the organic solvent is a C1-C5 alcohol or a $C_6$ arylene. Exemplary solvents include methanol, ethanol, isopropanol, propanol, butanol, toluene, xylene, and mixtures thereof. The organic solvent is typically added in the amount specific to the sol-gel precursor composition used. For example, for compositions comprising TEOS, water, and an organic solvent, the molar ratios of the TEOS:Water:Organic Solvent components are: 1:1-4:1-2 or 1:1-3:1. For example, in some embodiments, when ethanol is used as an organic solvent, the sol-gel precursor composition includes TEOS:Water:Ethanol in the molar ratios of 1:1:1, 1:2:1, 1:3:1, or 1:4:1. In other embodiments, when isopropanol is used, the sol-gel precursor composition includes TEOS:Water:Isopropanol in the molar ratios of 1:1:1, 1:2:1, 1:3:1 or 1:4:1. Typically, water with a pH in the range of 0-4 is used in the sol-gel precursor compositions.

In some embodiments, the sol-gel precursor compositions do not include an organic solvent. In some embodiments, the sol-gel precursor compositions further include an acid or base suitable to catalyze the hydrolysable gelation of the ceramic precursor. In some embodiments, a component of the ceramic precursor comprises a basic group or an acidic group that can serve as a gelation catalyst. For example, PSS comprises sulfonic acid groups suitable to act as an acid catalyst for gelation of sol-gel precursor compositions comprising TEOS and aqueous solutions of PSS, as demonstrated in the Examples.

In certain embodiments, the sol-gel precursor composition comprises (a) a ceramic precursor, such as silica (e.g., siloxane), ormosils, titania, germania, zirconia, alumina, graphite, silicon carbide, silicon nitride, boron nitride or others, and (b) optionally a solvent, such as an alcohol (e.g., methanol, ethanol, isopropanol, butanol, etc.) or an aromatic (e.g., toluene, xylene, etc.). The mixture of these two components typically accounts for about 30 volume % or less of the sol-gel precursor composition, about 20 volume % or less of the sol-gel precursor composition, or about 10 volume % or less of the sol-gel precursor composition. In some embodiments, the sol-gel precursor composition further comprises water in the amount of about 40 volume % or less of the sol-gel precursor composition, about 30 volume % or less of the sol-gel precursor composition, or about 20 volume % or less of the sol-gel precursor composition.

In some embodiments, the sol-gel precursor composition or a pre-treatment composition is a solution, gel or slurry comprising water and/or solvent: such as alcohols (e.g., methanol, ethanol, isopropanol, butanol, etc.) or aromatics (e.g., toluene, xylene, etc.) present in the amount of about 80 volume % or less of the composition, about 60 volume % or less of the composition, or about 50 volume % or less of the composition. Additionally, the sol-gel precursor composition or a pre-treatment composition comprises a colloidal suspension or a nanoparticle dispersion of ceramics (e.g. silica, titania, germania, alumina, etc.), present in the amount of about 50 volume % of the composition, about 40 volume % of the composition, or about 20 volume % of the composition.

In some embodiments, a post-treatment composition, e.g., chemical bath for dipping the sol-gel material comprises water and an acid, such as sulfuric acid, hydrochloric acid, phosphoric acid, nitric acid, methansulfonic acid, polystyrene sulfonic acid, acetic acid, or a mixture thereof. The acid concentrations typically are between about 10 M and about 0.1 M, or between about 2.5 M and about 0.5 M. The post-treatment composition can further comprise salts containing cationic groups such as sodium, calcium, lithium, ammonium, or magnesium and anionic groups such as chloride, bromide, carbonate, sulfate, sulfonate, iodide, phosphate, nitrite, nitrate, chlorate, borate, thiocyanate, thiosulfate and sulfide. Typically, the salt concentration is between about 1 M and about 0.01 M or between about 1 M and about 0.1 M.

Any suitable gelation method can be used to form the material disclosed herein from the components described above. For example, in some embodiments, gelling the sol-gel precursor compositions comprises chemical gelation, including hydrolyzing chemical gelation, non-hydrolyzing chemical gelation, and combinations thereof.

In one embodiment, chemical gelation comprises exposing the sol-gel precursor composition to an acid solution. In one embodiment, the acid solution is greater than 0.001 N. In one embodiment, the acid solution is greater than 1 N. In one embodiment, the acid solution is greater than 3 N. Suitable acids can be selected from the group consisting of sulfuric acid, nitric acid, acetic acid, hydrochloric acid, methane sulfonic acid, and phosphoric acid.

In some embodiments, the nanoporous matrix comprises a nanoporous transition metal oxide. Exemplary metal oxides include, but are not limited to, titanium dioxide (titanium(IV) oxide), $TiO_2$; titanium(II) oxide (titanium monoxide), TiO, a non-stoichiometric oxide; titanium(III) oxide (dititanium trioxide), $Ti_2O_3$; vanadium(II) oxide (vanadium monoxide), VO; vanadium(III) oxide (vanadium sesquioxide or trioxide), $V_2O_3$; vanadium(IV) oxide (vanadium dioxide), $VO_2$; vanadium(V) oxide (vanadium pentoxide), $V_2O_5$; chromium(II) oxide, CrO; chromium(III) oxide, $Cr_2O_3$; chromium dioxide (chromium(IV) oxide), $CrO_2$; chromium trioxide (chromium(VI) oxide), $CrO_3$; chromium (VI) oxide peroxide, $CrO_5$; manganese(II) oxide, MnO; manganese(II,III) oxide, $Mn_3O_4$; manganese(III) oxide, $Mn_2O_3$; manganese dioxide, (manganese(IV) oxide), $MnO_2$; manganese(VI) oxide, $MnO_3$; manganese(VII) oxide, $Mn_2O_7$; iron(II) oxide, FeO; iron(II) dioxide, $FeO_2$; iron(III) oxide, $Fe_2O_3$; cobalt(II) oxide, CoO; cobalt(III) oxide, $Co_2O_3$; nickel(II) oxide, NiO; nickel(III) oxide, $Ni_2O_3$; copper(I) oxide, $Cu_2O$; copper(II) oxide, CuO; copper peroxide, $CuO_2$; copper(III) oxide, $Cu_2O_3$; zinc oxide, ZnO; and mixed valence species or combinations thereof. In one embodiment, the metal oxide further comprises a corresponding metal hydroxide or a metal salt.

In some embodiments, the nanoporous ceramic matrix is made by sintering, cold-sintering, cementation, or precipitation form solution of alkali resistant and electrically insulating ceramic powders or particles having a mean particle size of less than 50 nm. Exemplary powders include nanosilica, nano-clay, silicate minerals, mullite, transition metal oxides, silicon carbide (SiC) and tungsten carbide (WC).

In some embodiments, the nanoporous matrix comprises a nanoporous polymer material.

In some embodiments, the nanoporous polymer material comprises an ethylene-based polymer. Suitable ethylene-based polymers include, but are not limited to, DOWLEX Polyethylene Resins, TUFLIN Linear low Density Polyethylene Resins, ELITE Enhanced Polyethylene Resins (all available from The Dow Chemical Company), high density polyethylenes (d>0.96 g/cc), medium density polyethylenes (density from 0.935 to 0.955 g/cc), EXCEED polymers and ENABLE polymers (both from ExxonMobil), and LDPE EVA.

In one embodiment, the composition further comprises a propylene-based polymer. Suitable propylene-based polymers include polypropylene homopolymers, propylene/a-olefin interpolymers, and propylene/ethylene interpolymers.

In one embodiment, the composition further comprises a heterogeneously branched ethylene/α-olefin interpolymer, and preferably a heterogeneously branched ethylene/a-olefin copolymer. In one embodiment, the heterogeneously branched ethylene/a-olefin interpolymer, and preferably a heterogeneously branched ethylene/α-olefin copolymer, has a density from 0.89 to 0.94 g/cc, or from 0.90 to 0.93 g/cc. In a further embodiment, the composition comprises 10 to 50 weight percent, or 20 to 40 weight percent, of the ethylene-based polymer, based on the weight of the composition.

Exemplary polymers include but not limited to polydimethylsiloxane (PDMS), polyurethane, polymethylmethacrylate (PMMA), polystyrene, cellophane, polyethylene, Polytetrafluoroethylene, poly(propylene), poly(vinyl chloride) (PVC), poly(hydroxyethyl methacrylate) (pHEMA), poly (ethylene terephthalate), polyether ether ketone (PEEK), polyether sulfone (PES), Nylon 6.6, high density polyethylene (HDPE), ultra high molecular weight polyethylene (UHMWPE), Highly crosslinked polyethylene (HXPE), Poly(ethylene glycol) (PEG), expanded PTFE (ePTFE), Poly(vinylpyrrolidone) (PVP), Poly(styrene-b-isobutylene-b-styrene) (SIBS), ethylene tetrafluoroethylene (ETFE), fluorinated ethylene propylene (FEP), tetrafluoroethylene (TFE), perfluoroalkoxy alkanes (PFA), fluorinated polypropylene (FLPP), low-density polyethylene (LDPE), polypropylene (PP), polyvinyl chloride (PVC), and combinations, mixtures, copolymers, and/or block copolymers thereof. In one embodiment, the polymer material comprises polyarylenes, polyarylenevinylenes, polyaryleneethylnylene, polyfluorenes, polyanilines, polythiophenes, polypyrroles, and any conjugated co-polymers. In one embodiment, the polymer material comprises a mixture, co-polymer, or block co-polymer of any combination of polymeric materials disclosed herein, in any ratio, any chain length, any degree of linearity, any polydispersity index, and having any degree of cross-linking.

Further exemplary polymers include, but are not limited to, polyethylene glycol; ethylene glycol; polypropylene glycol; polylactic acid; polyvinyl methyl ether; polyvinyl ethyl ether; polyvinyl alcohol; polyvinyl esters such as polyvinyl acetate and poly(vinyl cinnamate); polyvinylpyrrolidone; polyacrylics and polyacrylates such as polyhydroxypropyl acrylate, poly(methyl acrylate), poly (methyl methacrylate), polyacrylic acid; polyesters such as polyglycolide, polyglycolic acid, polylactic acid, polycaprolactone, polyhydroxyalkanoate, polyhydroxybutyrate, polyethylene adipate, polybutylene succinate, poly(3-hydroxybutyrate-co-3-hydroxyvalerate), polyethylene terephthalate, polybutylene terephthalate, polytrimethylene terephthalate, polyethylene naphthalate, and Vectran™; cellulose; unsaturated polyesters; methyl cellulose; hydroxyethyl cellulose; hydroxypropyl methyl cellulose; hydroxypropyl cellulose; ethyl hydroxyethyl cellulose; hydrophobically-modified cellulose; epoxy resins such as bisphenol A diglycidyl ether (DGEBA) resin, novolac epoxy resins, bisphenol E diglycidyl ether (DGEBE) resin, and bisphenol F diglycidyl ether (DGEBF) resin; triacetate polymers such as cellulose triacetate; dextran; hydrophobically-modified dextran; agarose; low-gelling-temperature agarose; latex; pectin; polyvinyl chloride; polypropylene; polyethylene; polystyrene; poly (ethylenimine); poly(ethylene glycol) (N) monomethacrylate; methylmethacrylate; poly(ethylene glycol) (N) monomethyl ether monomethacrylate; nylon; nylon 6; nylon 6,6; chitosan; rayon; polytetrafluoroethylene (Teflon/PTFE); expanded polytetrafluoroethylene (e-PTFE), thermoplastic polyurethanes; polyacrylamides; polyacrylonitriles; and combinations thereof. In one embodiment, the polymer is polylactic acid. In one embodiment, the polymer is polyvinylpyrrolidone. In one embodiment, the polymer is polystyrene. In one embodiment, the polystyrene is latex. In one embodiment, the latex is GF-3088 latex In some embodiments, the nanoporous polymer material comprises cross-linking polymers, wherein the polymers include multiplicity of side chains, such as, but not limited to, hyperbranched, dendritic, multiarm stars, hairy nanoparticles, brush polymers and comb products. Embodiments may include doping the polymers with cross-linking agents or using polymers with incorporated functional groups capable of causing cross-linking to inherently allow formation of networks. In certain embodiments, a substantial portion of the side chains have a molecular weight less than the main polymer chain.

In some embodiments, the nanoporous polymer material comprises a thermosetting polymer or a thermoplastic polymer. Examples of thermosetting polymers include, but are not limited to, epoxy resins, polyurethanes, silicones, unsaturated esters, phenolic resins and any other hydrocarbon based polymers that are capable of forming a three-dimensional cross-linked structure upon curing. In various embodiments, the thermosetting polymer comprises or consists of an epoxy resin. "Epoxy resin" may be any resin comprising epoxy groups. In specific embodiments, the thermosetting polymer comprises or consists of bisphenol epoxy resin, in particular bisphenol F epoxy resin.

In various embodiments, the thermosetting polymer has a glass transition temperature in the range of –30° C. to 120° C., such as in the range of –30° ° C. to 100° C., –30° C. to 60° C., –30° C. to 20° C., –30° ° C. to 0° C., 0° C. to 120° C., 0° C. to 80° C., 0° C. to 40° C., 0° C. to 20° C., 15° C. to 40° C., 20° C. to 120° ° C., 20° C. to 90° C., 20° C. to 50° C., 50° C. to 120° C., 50° C. to 90° C., or 60° ° C. to 90° C. In various embodiments, the glass transition temperature of the thermosetting polymer is in the range of 20° C. to 90° C.

The term "curing agent", as used herein, refers to a compound capable of initiating or catalyzing polymerization of a thermosetting resin to form a thermoset polymer with highly crosslinked networks. In various embodiments, the curing agent for the thermosetting resin is selected from polyfunctional amines, acids and acid anhydrides, phenols, alcohols and thiols. In embodiments wherein the thermosetting resin comprises or consists of an epoxy resin, the curing agent for the thermosetting polymer preferably comprises or consists of a phenalkamine.

The epoxy resin/curing agent concentration in the mixture may be in the range of about 5 wt % to about 100 wt %. For example, the epoxy/curing agent concentration in the mixture may be in the range of about 25 wt % to about 75 wt %, such as about 25 wt % to about 50 wt %, about 25 wt % to about 35 wt %, about 50 wt % to about 75 wt %, about 65 wt % to about 75 wt %, about 30 wt % to about 50 wt %, about 40 wt % to about 60 wt %, about 25 wt % to about 50 wt %, or about 75 wt %. In various embodiments, the epoxy/curing agent concentration in the mixture is in the range of about 25 wt % to about 75 wt %.

As used herein, the term "thermoplastic polymer" refers generally to a polymer that softens or melts when exposed to heat and returns to its original condition upon cooling. Examples of thermoplastic polymers include, but are not limited to, polystyrenes, polyolefins, polyamides, polyacrylates, polycarbonates, polyesters, polyether sulfones, polyether sulfides, polyether ketones, and mixtures thereof. In various embodiments, the thermoplastic phase or soft phase comprises or consists of a vinyl polymer formed by free radical polymerization of vinyl monomers. "Vinyl monomers", as used herein, relates to monomeric compounds that comprise a vinyl group, such as ethene, propene, butadiene, styrene, vinyl acetate, (meth)acrylic acid and esters thereof, and the like. In various embodiments, the thermoplastic monomers are vinyl monomers. In various embodiments, the thermosetting polymer, monomers of a thermoplastic polymer, and a curing agent for the thermosetting polymer may be present in liquid or melted state. It has to be noted that vinyl monomers also act as reactive diluents for viscous thermosetting resins, which avoids the use of volatile organic solvents and facilitates the emulsification process of thermosetting resins. Polymerization of the thermosetting polymer may be carried out at a temperature in the range of about 20° ° C. to about 85° C., such as about 20° C. to about 65° C., about 20° C. to about 45° C., about 20° ° C. to about 35° C., about 35° C. to about 85° C., about 50° C. to about 85° C., or about 60° C. to about 85° C.

In one embodiment, the thermoplastic or thermosetting polymer is a polyimide. "Polyimides" as used herein can include polyetherimides and polyamide imides having about 10 to about 1,000, or more specifically about 10 to about 500 units. Polyimides can be prepared by reacting a dianhydride, e.g., an aromatic bis(anhydride) with an organic diamine in an equimolar ratio to obtain a polyamic acid, which can form the polyimide upon further curing. The reaction can be carried out at an elevated temperature, in polar solvent suitable for dissolving the dianhydride and diamine comonomers.

Illustrative examples of aromatic bis(anhydride)s that can be used in the manufacture of polyimides include pyromellitic dianhydride, 2,3,6,7-naphthalene tetracarboxylic acid dianhydride, 3,3',4,4'-diphenyl tetracarboxylic acid dianhydride, 1,2,5,6-naphthalene tetracarboxylic acid dianhydride, 2,2',3,3'-diphenyl tetracarboxylic acid dianhydride, 2,2-bis(3,4-dicarboxyphenyl)propane dianhydride, bis(3,4-dicarboxyphenyl)sulfone dianhydride, 3,4,3,10-perylene tetracarboxylic acid dianhydride, bis(3,4-dicarboxyphenyl)ether dianhydride, 2,2-bis(2,3-dicarboxyphenyl)propane dianhydride, 1,1-bis(2,3-dicarboxyphenyl)ethane dianhydride, bis(3,4-dicarboxyphenyl)methane dianhydride, bis(2,3-dicarboxyphenyl)sulfone dianhydride, benzophenone tetracarboxylic acid dianhydride, cyclopentane tetracarboxylic acid dianhydride, cyclohexane tetracarboxylic acid dianhydride, butane tetracarboxylic acid dianhydride, 2,2-bis[4-(3,4-dicarboxyphenoxy)phenyl]propane dianhydride, 4,4'-bis(3,4-dicarboxyphenoxy)diphenyl ether dianhydride, 4,4'-bis(3,4-dicarboxyphenoxy)diphenyl sulfide dianhydride, 4,4'-bis(3,4-dicarboxyphenoxy)benzophenone dianhydride, 4,4'-bis(3,4-dicarboxyphenoxy)diphenyl sulfone dianhydride, 2,2-bis[4-(2,3-dicarboxyphenoxy)phenyl]propane dianhydride, 4,4'-bis(2,3-dicarboxyphenoxy)diphenyl ether dianhydride, 4,4'-bis(2,3-dicarboxyphenoxy)diphenyl sulfide dianhydride, 4,4'-bis(2,3-dicarboxyphenoxy)benzophenone dianhydride, 4,4'-bis(2,3-dicarboxyphenoxy)diphenyl sulfone dianhydride, 4-(2,3-dicarboxyphenoxy)-4'-(3,4-dicarboxyphenoxy)diphenyl-2,2-propane dianhydride, 4-(2,3-dicarboxyphenoxy)-4'-(3,4-dicarboxyphenoxy)diphenyl ether dianhydride, 4-(2,3-dicarboxyphenoxy)-4'-(3,4-dicarboxyphenoxy)diphenyl sulfide dianhydride, 4-(2,3-dicarboxyphenoxy)-4'-(3,4-dicarboxyphenoxy)benzophenone dianhydride, and 4-(2,3-dicarboxyphenoxy)-4'-(3,4-dicarboxyphenoxy)diphenyl sulfone dianhydride can be used, as well as a combination comprising at least one of the foregoing dianhydrides. Specifically useful dianhydrides include pyromellitic dianhydride and benzophenone tetracarboxylic acid dianhydride.

Diamines that can be reacted with the foregoing dianhydrides to form polyimides of formula (1) include, for example, ethylenediamine, propylenediamine, trimethylenediamine, diethylenetriamine, triethylenetetramine, hexamethylenediamine, heptamethylenediamine, octamethylenediamine, nonamethylenediamine, decamethylenediamine, 1,12-dodecanediamine, 1,18-octadecanediamine, 3-methylheptamethylenediamine, 4,4-dimethylheptamethylenediamine, 4-methylnonamethylenediamine, 5-methylnonamethylenediamine, 2,5-dimethylhexamethylenediamine, 2,5- dimethylheptamethylenediamine, 2,2-dimethylpropylenediamine, N-methyl-bis(3-aminopropyl) amine, 3-methoxyhexamethylenediamine, 1,2-bis(3-aminopropoxy) ethane, bis(3-aminopropyl) sulfide, 1,4-cyclohexanediamine, bis-(4-aminocyclohexyl) methane, m-phenylenediamine, p-phenylenediamine, 2,4-diaminotoluene, 2,6-diaminotoluene, m-xylylenediamine, p-xylylenediamine, 2-methyl-4,6-diethyl-1,3-phenylene-diamine, 5-methyl-4,6-diethyl-1,3-phenylene-diamine, benzidine, 3,3'-dimethylbenzidine, 3,3'-dimethoxybenzidine, 1,5-diaminonaphthalene, 1,4-diamino-2-phenylbenzene, 1,3-diamino-4-chlorobenzene, 3,3'-dimethoxybenzidine, m-xylenediamine, p-xylenediamine, 4,4'-diaminobiphenyl, 4,4'-diaminodiphenylmethane, 4,4'-diaminodiphenylpropane, 2,2-bis(4-aminophenyl)propane, 2,2-bis(4-aminophenyl)-1,1,1,3,3,3-hexafluoropropane, 3,4-diaminodiphenyl ether, 1,3-bis(3-aminophenoxy)benzene, 1,3-bis(4-aminophenoxy)benzene, 1,4-bis(4-aminophenoxy)benzene, 4,4'-bis(4-aminophenoxy)biphenyl, 4,4'-bis(3-aminophenoxy)biphenyl, 2,2-bis{4-(4-aminophenoxy)phenyl}propane, 2,2-bis {4-(4-aminophenoxy)phenyl}propane, 2,2-bis {4-(4-aminophenoxy)phenyl}-1,1,1,3,3,3-hexafluoropropane, 4,4'-diaminodiphenyl thioether, 4,4'-diaminodiphenyl sulfone, 4,4'-diaminodiphenyl ether, 2,2'-diaminobenzophenone, 3,3'-diaminobenzophenone, naphthalene diamines such as 1,8- and 1,5-diaminonaphthalene, heterocyclic aromatic diamines such as 2,6-diaminopyridine, 2,4-diaminopyrimidine, and 2,4-diamino-s-triazine, or siloxane-diamines such as bis(aminoalkyl)polysiloxanes, e.g., alpha, omega-(3-amino-1-propyl)polydimethylsiloxane. Mixtures comprising at least one of the foregoing diamines can also be used.

The reaction product of the dianhydride and the diamine is a polyamic acid polymer. A polyimide can be prepared from a polyamic acid polymer by heating at a temperature of about 150° C. to about 350° C., to complete the condensation to form the polyimide. Polyimide resins and polymers suitable for use herein have weight averaged molecular weights of about 2,000 to about 100,000, specifically about 3,000 to about 50,000, as determined by GPC. The polyimide polymers are flowable in a temperature range of interest for manufacture, specifically about 200° C. or less. Non-limiting examples of suitable aromatic polyimides include KAPTON® polyimide resin.

Other useful thermosetting resins for use in the polymer matrix include low molecular weight epoxy resins. Suitable epoxy resins can have weight averaged molecular weights (Mw) of about 2,000 to about 100,000, specifically about 3,000 to about 50,000, as measured, for example, by gel permeation chromatography (GPC); an epoxy equivalent weight (i.e., number averaged molecular weight per one epoxy) of from about 170 to about 2000; and a melting point below about 140° C. Combinations of epoxy resins can be used.

Specific examples of epoxy resins include epoxidized esters of polyethylenically unsaturated monocarboxylic acids, epoxidized esters of unsaturated monohydric alcohols and polycarboxylic acids, such as, for example, bis-(2,3-epoxybutyl) adipate, bis-(2,3-epxoybutyl)oxalate, bis-(2,3-epoxyhexyl)succinate, bis-(3,4-epoxybutyl)maleate, bis-(2,3-epoxyoctyl)pimelate, bis-(2,3-epoxybutyl)phthalate, bis-(2,3-epoxyoctyl)tetrahydrophthalate, bis-(4,5-epoxydodecyl)maleate, bis-(2,3-epoxybutyl)terephthalate, bis-(2,3-epoxypentyl)thiodipropionate, bis-(5,6-epoxytetradecyl)diphenyldicaboxylate, bis-(3,4-epoxyheptyl)sulfonyl-dibutyrate, tris-(2,3-epoxybutyl)-1,2,4-butanetricarboxylate, bis-(5,6-epoxypentadecyl)tartrate, bis-(4,5-epxoytetradecyl)

maleate, bis-(2,3-epoxybutyl)azelate, bis-(3,4-epoxybutyl) citrate, bis-(5,6-epoxyoctyl)cyclohexane-1,2-dicarboxylate, and bis-(4,5-epoxyoctadecyl)malonate; epoxidized esters of unsaturated alcohols and unsaturated carboxylic acids, such as 2,3-epoxybutyl-3,4-epoxypentanoate, 3,4-epoxyhexyl, 3,4-epoxypentanoate, 3,4-epoxycyclohexyl-3,4-epoxycyclohexanoate, 3,4-epoxycyclohexyl-4,5-epoxyoctanoate, and 2,3-epoxycyclohexylmethyl epoxycyclohexane carboxylate; epoxidized derivatives of polyethylenically unsaturated polycarboxylic acids, such as dimethyl-8,9,12,13-diepoxyeicosanedioate, dibutyl-7,8,11,12-diepoxyoctadecanedioate, dioctyl-10,11-diethyl-8,9,12,13-diepoxyeicosanedioate, dihexyl-6,7,10,11-diepoxyhexadecanedioate, didecyl-9-epoxy-ethyl-10,11-epoxyoctadecanedioate, dibutyl-3-butyl-3,4,5,6-diepoxycyclohexane-1,2-dicarboxylate, dicyclohexyl-3,4,5,6-diepoxycyclohexane-1,2-dicarboxylate, dibenzyl-1,2,4,5-diepoxycyclohexane-1,2-dicarboxylate, and diethyl-5,6,10,11-diepoxyoctadecyl succinate; epoxidized polyesters obtained by reacting an unsaturated polyhydric alcohol and/or unsaturated polycarboxylic acid or anhydride groups, such as for example, the polyester obtained by reacting 8,9,12,13-eicosanedienedioic acid with ethylene glycol, the polyester obtained by reacting diethylene glycol with 2-cyclohexene-1,4-dicarboxylic acid and the like, and mixtures thereof; and epoxidized polyethylenically unsaturated hydrocarbons, such as epoxidized 2,2-bis (2-cyclohexenyl)propane, epoxidized vinyl cyclohexene and epoxidized dimer of cyclopentadiene.

Epoxidized polymers and copolymers of diolefins, such as butadiene, can also be useful. Examples of these include epoxidized unsaturated butadiene-acrylonitrile copolymers (nitrile rubbers), epoxidized unsaturated butadiene-styrene copolymers, and the like.

Other useful epoxy resins include the glycidyl ethers and particularly the glycidyl ethers of polyhydric phenols and polyhydric alcohols. The glycidyl ethers of polyhydric phenols are obtained by reacting epichlorohydrin with the desired polyhydric phenols in the presence of alkali. Others include the polyglycidyl ether of 1,1,2,2-tetrakis-(4-hydroxyphenyl)ethane (with a melting point of 85° C.), the polyglycidyl ether of 1,1,5,5-tetralis-(hydroxyphenyl)pentane, and the like, and mixtures thereof. Further examples include the glycidylated novolacs obtained by reacting epichlorohydrin with the phenolic novolac resins obtained by the condensation of formaldehyde with a molar excess of a hydroxyaromatic compound such as phenol or cresol.

Suitable curing agents for epoxy resins include, for example, amines such as imidazole, aniline, ethanolamine, diethanolamine, triethanolamine, pyridine, and the like. These amines can be present as free amines or as their acid salts, where suitable acids include mineral acids such as hydrochloric, sulfuric, nitric acids, and the like; organosulfonic acids such as toluenesulfonic, methanesulfonic, trifluoromethanesulfonic acids, and the like; and carboxylic acids such as formic, acetic, propionic, cyclohexanecarboxylic, benzoic, adipic, malonic, maleic, fumaric acids and the like. Combinations of the foregoing can be used. Anhydrides can also be used, such as maleic anhydride, itaconic anhydride, benzoic acid anhydride, acetic anhydride, adipic anhydride, combinations thereof, and the like.

In some embodiments, the nanoporous material comprises a fluoropolymer. Examples of fluoropolymers that can be used include polytetrafluoroethylene (PTFE), perfluoropolyvinyl acetate (PFA), perfluoro polyvinyl alcohol, and the like, and a combination comprising at least one of the foregoing. In addition, copolymers such as poly(tetrafluoroethylene)-co-(trifluorovinylacetate), poly(tetrafluoroethylene)-co-(trifluorovinylalcohol), and the like, and a combination comprising at least one of the foregoing, can also be used. Where used, fluoropolymers are desirably processable such that they can be coated either as a suspension of crosslinkable particles, or as a melt, and are functionalized such that the fluoropolymer can be crosslinked using appropriate crosslink chemistry. Suitable functional groups include alcohols, phenols, amines, anhydrides, carboxylic acid derivatives, and the like. Suitable crosslinking agents for use with fluoropolymers include epoxy compounds, precursors to aromatic ethers such as 4,4'-difluorodiphenylether, 4,4'-difluorodiphenylsulfone, and bis(4,4'difluorophenyl)isopropylidene; dianhydrides such as pyromellitic dianhydride; and the like. The fluoropolymers can also be crosslinked by a free radical mechanism using pendant vinyl groups and a free radical curing agent.

Silicones can also be used as a thermosetting resin composition in the polymer material. Suitable silicones are derived from the reaction of an organopolysiloxane having at least two alkenyl groups per molecule and an organopolysiloxane having at least two hydrogen groups per molecule. Organopolysiloxanes having at least two alkenyl groups per molecule are generally represented by the formula: MaDb TeQd, wherein the subscripts a, b, c, and d are zero or a positive integer, subject to the limitation that if subscripts a and b are both equal to zero, subscript c is greater than or equal to two; M has the formula $R_3SiO_{1/2}$; D has the formula $R_2SiO_{2/2}$; T has the formula $RSiO_{3/2}$; and Q has the formula $SiO_{4/2}$, wherein each R group independently represents alkenyl groups, substituted and unsubstituted monovalent hydrocarbon groups having from one to forty, specifically one to six carbon atoms each, subject to the limitation that at least two of the R groups are alkenyl groups. Suitable alkenyl R-groups are exemplified by vinyl, allyl, butenyl, pentenyl, hexenyl, and heptenyl, with vinyl being particularly useful. The alkenyl group can be bonded at the molecular chain terminals, in pendant positions on the molecular chain, or both.

Other silicon-bonded organic groups in the organopolysiloxane having at least two alkenyl groups, when present, are exemplified by alkyl groups such as methyl, ethyl, propyl, butyl, pentyl, and hexyl; aryl groups such as phenyl, tolyl, and xylyl; arylalkyl groups such as benzyl and phenethyl; and halogenated alkyl groups such as 3-chloropropyl and 3,3,3-trifluoropropyl. Methyl and phenyl are specifically useful.

The alkenyl-containing organopolysiloxane can have straight chain, partially branched straight chain, branched-chain, or network molecular structure, or can be a mixture of such structures. The alkenyl-containing organopolysiloxane is exemplified by trimethylsiloxy-endblocked dimethylsiloxane-methylvinylsiloxane copolymers; trimethylsiloxy-endblocked methylvinylsiloxane-methylphenylsiloxane copolymers; trimethylsiloxy-endblocked dimethylsiloxane-methylvinylsiloxane-methylphenylsiloxane copolymers; dimethylvinylsiloxy-endblocked dimethylpolysiloxanes; dimethylvinylsiloxy-endblocked methylvinylpolysiloxanes; dimethylvinylsiloxy-endblocked methylvinylphenylsiloxanes; dimethylvinylsiloxy-endblocked dimethylvinylsiloxane-methylvinylsiloxane copolymers; dimethylvinylsiloxy-endblocked dimethylsiloxane-methylphenylsiloxane copolymers; dimethylvinylsiloxy-endblocked dimethylsiloxane-diphenylsiloxane copolymers; and mixtures comprising at least one of the foregoing organopolysiloxanes.

A suitable organopolysiloxane having at least two silicon-bonded hydrogen atoms per molecule is generally represented by the formula: $M'_aD'_bT'_cQ'_d$, wherein the subscripts a, b, c, and d are zero or a positive integer, subject to the limitation that if subscripts a and b are both equal to zero, subscript c is greater than or equal to two; M' has the formula $R'_3SiO_{1/2}$; D' has the formula $R'_2SiO_{2/2}$; T' has the formula $R'SiO_{3/2}$; and Q' has the formula $SiO_{4/2}$, wherein each R' group independently represents hydrogen, substituted and unsubstituted monovalent hydrocarbon groups having from one to forty, specifically one to six carbon atoms each, subject to the limitation that at least two of the R' groups are hydrogen. Specifically, each of the R' groups of the organopolysiloxane having at least two silicon-bonded hydrogen atoms per molecule are independently selected from hydrogen, methyl, ethyl, propyl, butyl, pentyl, hexyl, aryl, phenyl, tolyl, xylyl, arylalkyl, benzyl, phenethyl, halogenated alkyl, 3-chloropropyl, 3,3,3-trifluoropropyl, and combinations comprising at least one of the foregoing. Methyl and phenyl are specifically preferred.

In one embodiment, the nanoporous polymer material comprises an organopolysiloxane component which can have straight chain, partially branched straight chain, branched-chain, cyclic, or network molecular structure, or can be a mixture of two or more selections from organopolysiloxanes with the exemplified molecular structures.

The hydrogen-containing organopolysiloxane is exemplified by trimethylsiloxy-endblocked methylhydrogenpolysiloxanes; trimethylsiloxy-endblocked dimethylsiloxane-methylhydrogensiloxane copolymers; trimethylsiloxy-endblocked methylhydrogensiloxane-methylphenylsiloxane copolymers; trimethylsiloxy-endblocked dimethylsiloxane-methylhydrogensiloxane-methylphenylsiloxane copolymers; dimethylhydrogensiloxy-endblocked dimethylpolysiloxanes; dimethylhydrogensiloxy-endblocked methylhydrogenpolysiloxanes; dimethylhydrogensiloxy-endblocked dimethylsiloxanes-methylhydrogensiloxane copolymers; dimethylhydrogensiloxy-endblocked dimethylsiloxane-methylphenylsiloxane copolymers; and dimethylhydrogensiloxy-endblocked methylphenylpolysiloxanes.

In some embodiments, the nanoporous polymer material comprises a covalent organic framework with stable ordered nanopores. Covalent organic frameworks (COFs) due to their ordered structure, porosity and high surface area serve as crystalline organic supports and find use in several applications. The organic backbone can be manipulated to introduce specific functional groups and thereby specific chemical characteristics.

In one embodiment, the COFs comprise a plurality of amine subunits selected from the group consisting of diamines, triamines, and tetraamines; and a plurality of aldehyde subunits selected from the group consisting of dialdehydes, trialdehydes, and tetraaldehydes, where each di-, tri-, or tetraamine subunit is bonded with at least one aldehyde subunit by an imine bond. In one embodiment, iminic nitrogens are located at the cavities of the COFs and can be further functionalized with a metal atom selected from the group consisting of Mn, Fe, Co, Ni, Ru, Pt, Pd, Rh, Ir, Au, Nd, Eu and mixtures thereof, which confers to the material added chemical, electronic, magnetic, optical and redox features.

In one embodiment, the covalent organic framework is flexible. In one embodiment, the COF comprises sp3 nitrogen. In one embodiment, the monomer contains tetrahedral nitrogen covalently linked to three p-benzaldehyde units which are completely free to rotate providing flexibility around the tetrahedral nodes, while the lone-pairs on the nitrogen center make it electronically active. In one embodiment, The covalent organic framework comprises Tris(4-formylphenyl)amine as monomer. In one embodiment, the COF$_2$ is in the β-phase and forms nano composite with homometallic or heterometallic nanoparticles.

In one embodiment, the covalent organic framework comprises a plurality of phthalocyanine catechol subunits comprising a phthalocyanine moiety and at least two catechol moieties, and a plurality of multifunctional linker groups comprising boron, wherein a plurality of distinct phthalocyanaine catechol subunits are bonded to at least one multifunctional linker by boronate ester bonds. In an embodiment, the phthalocyanine subunit comprises a metal atom or metal ion. % In an embodiment, the framework has pores having a diameter of 2 nm to 20 nm, wherein the pores run parallel to the stacked aromatic moieties. In an embodiment, the framework is a crystallite, where the longest dimension of the crystallite is from 50 nm to 10 microns. In an embodiment, the framework is thermally stable at temperatures of from 20° C. to 500° C. In an embodiment, the framework absorbs light having a wavelength of 200 nm to 1500 nm.

In some embodiments, the covalent organic framework exhibits a water adsorption capacity of about 50-80 milligrams water per gram of the covalent organic framework. In some aspects, a water contact angle on the covalent organic framework is about 150° or more. In one embodiment, the covalent organic framework is highly oleophillic. In some aspects, the covalent organic framework exhibits a toluene adsorption capacity of about 500-800 milligrams toluene per gram of the covalent organic framework. In some aspects, a nitrobenzene contact angle on the covalent organic framework is about 10° or less.

In one embodiment, the covalent organic framework is incorporated into a variety of compositions. In some aspects, the composition includes a polymeric foam matrix having a three-dimensional network of polymer fibers; and a covalent organic framework encasing at least a portion of the polymer fibers. The polymeric foam matrix can include a foam selected from polyurethane foam, polyurea foam, polyvinyl chloride foam, polypropylene foam, polyethylene foam, polystyrene foam, polyvinyl acetate foam, and melamine foam. The covalent organic framework can be intertwined within the polymeric foam matrix such that the covalent organic framework encasing the portion of the polymer fibers is stable to mechanical compression of the polymeric foam matrix. The covalent organic framework can be intertwined within the polymeric foam matrix such that the polymeric foam matrix maintains about the same level of mechanical compressibility as the otherwise same polymeric foam matrix except without the covalent organic framework. The covalent organic framework can also be part of or form a surface coating. For example, in some aspects a droplet is provided having an aqueous central region surrounded by an outer surface of a covalent organic framework described herein.

Moreover, in certain embodiments, the covalent organic framework comprises COF-1, COF-5, COF-6, COF-8, COF-10, COF-11A, COF-14A, COF-16A, COF-18A, COF-42, COF-43, COF-66, COF-366, TP-COF, NiPc-PBBA COF, CTF-0, CTF-1, HTTP-DBP COF, ZnPc-Py COF, ZnPc-DPB COF, ZnPc-NDI COF, ZnPc-PPE COF, TpPa-1, or TpPa-2, TpPa-NO$_2$, TpBD-(NO$_2$)$_2$, TpBD-Me$_2$, TpPa-F$_4$, TpBD-OMe$_2$, TpBD, DhaTph COF, TAPB-TFP COF, iPr-TAP-TFP, TAPB-TFPB, ILCOF-1, DAAQ-TFP COF, TAPB-PBA COF, HPB COF, HCB COF, H$_2$P-COF, Ph-An-COF, Tp-Azo COF, TP-PirDI COF, Py-Azine COF, CS COF, CuP-SQ COF, CuP-Ph COF, CuP-TFPh COF, Star-COF, CuPc-COF, CoPc-COF, NiPc BTDA COF, ZnP-COF, Ppy-COF, 1-S COF, 1-Se COF, 1-Te COF, T-COF 1, T-COF 2, T-COF 3, T-COF 4, NTU-COF-1, NTU-COF-2, APTES-COF-1, FCTF-1 COF, TRITER-1, TDCOF-5, BLP-2 COF, TpTP-H, TpTP-OEt, TpTP-OMEG, TpTP-ODEG, or TpTP-OTEG In certain embodiments, the covalent organic framework has hexagonal symmetry; trigonal symmetry, tetragonal symmetry, rhombohedral symmetry, orthorhombic symmetry, monoclinic symmetry, or triclinic symmetry.

In addition, the covalent organic framework may further comprise a lithium salt. In specific embodiments, covalent organic framework further comprises LICIO4, LiPF$_6$, LIBF4, Li(CF$_3$SO$_3$), Li[N(CF$_3$SO$_2$)$_2$], Li[N(CF$_3$CF$_2$SO$_2$)$_2$], LiAsF$_6$, LiH, Li(n-C$_4$H$_5$), LiCH$_3$, Li(½ri-C4H5), Li(CeH5), or Li$_2$CO$_3$, or combinations thereof.

The covalent organic framework may contain functional groups chosen from alkyl chains, oligo- and poly ethers, fluorinated alkyl chains, alkyl chains containing anionic groups, alkyl chains containing sulfonate groups, alkyl chains containing carboxylate groups, imides, or anionic group.

In some embodiments, the nanoporous polymer material further comprises one or more additives. Additives include, but are not limited to, stabilizers, plasticizers, antistatic agents, pigments, dyes, nucleating agents, fillers, slip agents, fire retardants, processing aids, smoke inhibitors, viscosity control agents and anti-blocking agents. The polymer composition may, for example, comprise less than 10 percent (by the combined weight) of one or more additives, based on the weight of the nanoporous polymer material.

In one embodiment, the nanoporous polymer material is treated with one or more stabilizers, for example, antioxidants, such as IRGANOX 1010, IRGANOX 1076 and IRGAFOS 168 (Ciba Specialty Chemicals; Glattbrugg, Switzerland). In general, the nanoporous polymer material is treated with one or more stabilizers before extrusion or other melt processes. Processing aids, such as plasticizers, include, but are not limited to, the phthalates, such as dioctyl phthalate and diisobutyl phthalate, natural oils such as lanolin, and paraffin, naphthenic and aromatic oils obtained from petroleum refining, and liquid resins from rosin or petroleum feedstocks. Exemplary classes of oils, useful as processing aids, include white mineral oil such as KAYDOL oil (Chemtura Corp.; Middlebury, Conn.) and SHELLFLEX 371 naphthenic oil (Shell Lubricants; Houston, Tex.). One other suitable oil is TUFFLO oil (Lyondell Lubricants; Houston, Tex).

Blends and mixtures of the nanoporous polymer material with other polymers may be performed. Suitable polymers for blending with the nanoporous polymer material include natural and synthetic polymers. Exemplary polymers for blending include propylene-based polymers (both impact modifying polypropylene, isotactic polypropylene, atactic polypropylene, and random ethylene/propylene copolymers), various types of ethylene-based polymers, including high pressure, free-radical LDPE, Ziegler-Natta LLDPE, metallocene PE, including multiple reactor PE ("in reactor" blends of Ziegler-Natta PE and metallocene PE, ethylene-vinyl acetate (EVA), ethylene/vinyl alcohol copolymers, polystyrene, impact modified polystyrene, ABS, styrene/butadiene block copolymers and hydrogenated derivatives thereof (SBS and SEBS), and thermoplastic polyure thanes. Homogeneous polymers, such as olefin plastomers and elastomers, ethylene and propylene-based copolymers (for example, polymers available under the trade designation VERSIFY Plastomers & Elastomers (The Dow Chemical Company) and VISTAMAXX (ExxonMobil Chemical Co.)

can also be useful as components in blends comprising the nanoporous polymer material).

In some embodiments, the nanoporous material further comprises a coating. For example, the coating may improve the stability of the material to pore solution conditions. In other embodiments, the coating may prevent salt crystallization on the surface of the material, or may affect the transfer of pore solution in and out of the nanoporous housing. It would be desirable in many circumstances to provide durable, submicrosocopically thin, substantially invisible coatings to nanoporous material to alter the physical and chemical properties of the surfaces. For example, it may be desirable to impart properties such as lubricity (and thus, improved mar resistance), anti-stick (and thus, improved cleanability, a degree of self-cleaning, and resistance to the attachment of organic growths), or improved resistance to chemical attack by physically warding off contact with corrosive materials which may be present in the environment. For example, the ability to modify or profoundly change one or more surface properties while retaining other desired functional properties of a substrate is desirable for a wide range of substrates and devices.

In some embodiments, the coated nanoporous material has modified surface properties. In one embodiment, the coating comprises a substantially monomolecularly thin, randomly oriented (i.e., substantially noncrystalline, amorphous) layer of flexible polymer chains having a plurality of chain ends, and means for bonding the ends of the polymer chains of the layer to the material. In one embodiment, relatively long polymer chains are deployed on the surface of the material so as to be free to fluidly respond to physical deformation forces applied to their exposed outer surface, while being firmly attached to the substrate at the respective ends of the chains. In this connection, the chains may be attached (at their ends by chemical bonds) to a relatively much more polar bonding layer adherent to the material. The bonding layer at the time of application may be in the form of attached monomeric or oligomeric polymer chain units, thereby endowing an ease of application, from solution, by a surface-self-attachment process, in the generally-known manner of surface-active agents, but in which the intermediate polymer chain has a substantially noncrystalline, amorphous structure rather than being an ordered, or crystalline array.

In one embodiment, the nanoporous material may be provided with desirable and unusual characteristics such as extremely low static friction coefficients and/or very low hysteresis of wetting and desiccation by liquids. A wide variety of chain polymers, such as including but not limited to any polymer described elsewhere herein, can serve the function of a monomolecular coating.

A variety of side groupings may be present on the chains providing that they do not too adversely affect fluidity and chain flexibility. Thus, for example, the methyl groups attached to a polysiloxane backbone may, in certain instances, be advantageously replaced in part or wholly by other groupings, and for example, for some purposes it may be advantageous to replace hydrogen atoms of, say an aliphatic or other hydrocarbon backbone chain polymer with, for example, fluorine atoms, or such like, all without departing from the basic requirements for the chain polymers used monomolecular coating. Resistance to chemical chain scission, including simple hydrolysis, is increased by several orders of magnitude if the -silicone-oxygen-silicone-bonding sequence commonly used as the backbone chains in silicone polymers is replaced by a $-(carbon)_x$ -silicone-$(carbon)_y$- type of sequence, wherein x and y are low value integers, including one, and are not necessarily identical or even constant along the length of a given chain.

In the preparation of suitable monomolecular coating materials for providing loop-bonded amorphous surface coatings, relatively highly polar end groups may be provided at the ends of the chain polymer which are of a type co-reactive with the chain polymer's end groups to permit the chemical joining of the chain polymer and the end groups, as previously indicated. In another method of preparation, the materials may be so chosen that they serve as initiators and also as terminators of a chain polymerization reaction used in preparing the long chain polymer, becoming attached at each end in the process. In either case, these polar groups should best be such as to be both attracted to and then to bond to the substrate which is to be treated, the latter most preferably, though not necessarily, being by chemical rather than mere physical bonds. The number of available materials which can serve as the polar groups, or means for chemically bonding the chain ends to the substrate, is quite large, and choice will depend upon the intended conditions of use, including the nature of the substrate to which it is to be attached as well as the nature of the end groupings on the chain polymer, to enable secure attachment by chemical bonding. Epoxy-reactive monomers and oligomers can serve well as the polar groups, as can urethane types. Poly (monomethyl siloxane) polymers of low molecular weight, with or without the addition of small amounts of di- and trimethyl siloxane monomer units, generally work particularly well, especially with silicone-type chain polymers. Though silicone-attached hydroxyl (OH) groups would, in principal, be satisfactory for causing the latter to bond to a wide variety of material, considerations of storage stability suggest that they be replaced (temporarily, in effect) by halogen, amine, acetoxy, alkoxy(e.g., methoxy), or similar groups, these being listed in descending order both of deleterious sensitivity to pre-reaction with stray (ambient) moisture before use, as well as the desired reactivity with active sites on the substrate. Upon reaction (e.g., such as with surface silanol groups of a substrate such as a glass substitute), these materials liberate, respectively, in the order listed, halogen, acids, ammonia (or amines), acetic acid, and methanol. Higher organic acids and alcohols can be substituted for the acetoxy and methoxy groups if desirable, but rate of cure will be greatly decreased with increasing molecular size of such alternate. In each case, the silicon-attached radical is replaced by a hydroxyl group. This, in turn, can react with active sites on the material surface, thereby firmly attaching the polar end groups to that surface. Typical of the reactive groups found on such surfaces are the hydroxyl groups present on most metal, glass and ceramic surfaces and, to a greater or lesser extent, on various organic polymer surfaces. The latter may be chemically characteristic of the material, as with cellulose and phenolics, or the result of surface degradation reactions (polyesters, alkyds, and surface oxidation products) or surface-seeking defect sites arising from the interior of materials normally not so provided. Similarly, and for the same reasons, organics may possess residual aldehyde or carboxyl groups, or double bonds which are subject to surface oxidation. All may combine with capped, reactive silane groups at the chain polymer ends or silicon-attached hydroxyls to split out water and leave the silicon atom oxygen-bonded to the surface. Double bonds themselves can react also, but do so more readily with properly catalyzed silicon halides, as do free amine groups on protein and nylon surfaces. Epoxies react with these and with carboxyl groups, as do urethanes and urethanes also react well with surface hydroxyl groups. The literature on chemicals, plastics, coatings and tie coats, and especially that on coupling agent additives for use in adhesives or composites, is replete with information concerning securing and facilitating attachment of fluid-applied materials to membranes in general and to specific nanoporous materials in particular.

In some embodiments, the monomolecular coating is effected by treating surface hydroxy groups on the nanoporous material (i.e., the substrate) with a suitable crosslinking agent. In one embodiment, the crosslinking agent comprises a chlorosilane. By contacting the substrate material with a non-aqueous organic solvent solution of a compound having a fluoroalkyl group and a reactive silane group, a reaction between the active hydrogen in the hydrophilic groups of the substrate surface and the reactive silane groups occurs to form a monomolecular film bonded via —SiO— groups (i.e., a covalently bonded film). Such a reaction is called a chemical adsorption reaction, and the monomolecular film obtained in this way is called a chemically adsorbed single molecular (or unimolecular or monomolecular) film. When this chemically adsorbed monomolecular film is coupled via firm chemical bonds to a real image side mirror surface, its adhesion is so strong that usually it is not separated unless the surface of the substrate is cut away. Since the compound has a hydrophobic group at the other end, this hydrophobic property provides a contamination-free effect.

In some embodiments, such as in cases where the nanoporous material does not have a sufficient number of hydrophilic groups, it may be rendered hydrophilic by means such as electron or ion beam irradiation in an oxygen or nitrogen atmosphere.

The molecule constituting the chemically adsorbed monomolecular film may be a silane-based surface active compound having a chlorosilane ($—SiCl_v \, Y_{3-v}$) group or an alkoxysilane ($Si(OW)_v \, Y_{3-v}$) group at one end and a fluorine-substituted alkyl group at the other end. In the above formulas, v represents an integer ranging from 1 to 3, Y represents a hydrogen atom or a lower alkyl (for example $C_1$ to $C_6$) or lower alkoxy group (for example $C_1$ to $C_6$), and W represents a lower alkyl group. Among the silane-based surface active compounds mentioned above, chlorosilane-based surface active compounds are preferred, since they can reliably undergo a chemical adsorption reaction to form a chemically adsorbed monomolecular film at normal temperature. Among the chlorosilane-based surface active compounds, those having a trichlorosilane group (v is 3) is preferred because siloxane bounds intervene between adjacent adsorbed molecules. Further, in order to increase the concentration of the adsorbed molecules, the silane-based surface active compound having a straight chain is preferred. Examples of especially preferred chlorosilane-based surface active compounds are those represented by the formula: $CF_3—(CF_2)_t—(R^2)_r-SiCl_v \, Y_{3-v}$, where t is an integer of at least 3, preferably 3 to 10, r is 0 or 1, $R^2$ is an alkylene group of at least one (preferably 1 to 20) carbon atoms which may contain a vinylene (—CH—CH—), ethynylene (—C≡C—) group or may be interrupted by a COO group or by a silicon or oxygen atom, and Y is a hydrogen atom, a lower alkyl group (for example $C_1$ to $C_6$) or lower alkoxy group (for example $C_1$ to $C_6$), and v is an integer ranging from 0 to 2. Preferably, those chlorosilane-based surface active compounds have 12 to 22 carbon atoms. More specific examples include: $CF_3(CF_2)—(CH_2)_2SiCl_3$, $CF_3(CF_2)_3(CH_2)_2Si(CH_3)_2(CH_2)_9SiCl_3$, and $CF_3(CF_2)_5(CH_2)_2SiCl_3$.

In some embodiments, $R^2$ in the surface active compounds above contains a vinylene or ethynylene group. In one embodiment, causing a polymerization of unsaturated bonds with a catalyst or with light or high energy ray irradiation, intra-molecular bonds may be produced, which result in a firmer monomolecular film.

In one embodiment, the chemically adsorbed monomolecular film may be either a single monomolecular layer or a lamination of two or more monomolecular layers. In the latter case, however, it may be necessary that there are chemical bonds between adjacent laminated layers. For producing such a lamination of monomolecular layers, one exemplary method is as follows. At first a chlorosilane-based surface-active compound having a group (such as a vinyl or ethynyl group) that can subsequently be converted to an active hydrogen-containing reactive group (such as a hydroxyl, imino or amino group) is used to form a monomolecular film. The convertible group is then converted to the active hydrogen-containing reactive group. To a surface thus treated, a chlorosilane-based surface-active compound is applied to form a hydrophobic monomolecular film.

In some embodiments, the nanoporous matrix material is stable in any aqueous conditions. In one embodiment, the nanoporous material is stable at a pH of 1, 2, 3, 4, 5, 6, 7, 8, 9, 10, 11, 12, 13, and/or 14, and in at any pH value therebetween. In one embodiment, the nanoporous material is stable at a pH of 13 or above.

In one embodiment, the nanoporous material comprises pores having an average size of 1, 2, 3, 4, 5, 6, 7, 8, 9, or 10 nm. In one embodiment, the pores have an average size of 1 nm to 100 nm. In one embodiment, the pores have an average size of 2 nm to 50 nm. In one embodiment, the pores have an average size of 3 nm to 25 nm. In one embodiment, the pores have an average size of 4 nm to 20 nm. In one embodiment, the pores have an average size of 5 nm to 10 nm.

In one embodiment, the nanoporous polymer material is coated with a metal oxide layer. Exemplary metal oxide coatings include, but are not limited to, the metal oxides disclosed elsewhere herein.

The sensor matrix may be composed of custom-designed nano-porous material or materials with controlled porosity, pore size, and formation factor. These materials include but are not limited to the following. In one embodiment, the sensor matrix is autoclaved concrete with water to cement (w/cm) ratio of 0.15 to 0.25, comprised of 500 to 800 grams of cement, 1 to 300 grams of silica flour, 1 to 300 grams of silica fume (densified, undensified, or slurry), 150 to 250 grams of water, and 1 to 6 milliliters of high-range water reducing admixture (HRWRA) where the sensor body is autoclaved with maximum temperature of 160 to 210° C. and 90 to 290 psia pressure, ramp up period of about 1 to 3 hours, holding period of 3 to 8 hours at maximum temperature, and cooling period of about 15 to 60 minutes. In one embodiment, the sensor matrix is dry-pressed alumina ceramics sintered under 100 to 150 MPa pressure and temperature of 1000 to 1300° C. The alumina powder is first mixed with a small amount of isopropanol to achieve good compaction. The mix is then pressed into pellets under 100 to 150 MPa pressure and temperature of 1000 to 1300° C. In one embodiment, the sensor matrix is dry-pressed mullite ceramics sintered under 100 to 150 MPa pressure and temperature of 1250 to 1600° C. β-alumina (<200 nm average particle size) and silica (>300 m²/g) are combined in 3:2 molar ratio. Mechanical activation is essential for the formation of mullite at lower temperatures (1250 to 1400° C.) by either hand grinding the components in a mortar and pestle or grinding the powder mixture with isopropanol in a micronizing mill with alumina grinding inserts for 10 to 30 minutes.

Sensor Electronic Assembly

The sensor can be manufactured with any desired number of electrodes, including two or four electrodes. Certain embodiments will include two or more electrodes. In one embodiment, the sensor has a four-electrode setup where the outer two electrodes carry the excitation current and the inner two electrodes measure the voltage difference. In one embodiment, the second pair of electrodes can also provide sensor diagnostics, which can then be used to compensate the measurement if scale or particulate build-up occur on electrodes (fouling).

In one embodiment, the wiring is attached to the terminals (electrodes) before attaching them to the sensor matrix. In one embodiment, the terminals and wiring are made of stainless steel, copper, or titanium. In one embodiment. the terminals are attached to the sensor matrix using conductive adhesives, which can be silver-filled two-component epoxy or polyurethane adhesives.

To secure the terminals to the outer surface of the sensor matrix, one of the following techniques can be used. In one embodiment, the frame accommodates an indent the same size as the terminals in the mold used for manufacturing the sensor matrix. In one embodiment, the autoclaved concrete, geopolymer, and polymer-based sensor matrix have silicon molds fabricated based on an original positive model that is created using either 3D printing with resins or injection molding with plastics. In one embodiment, the cylindrical sensor matrix shape has a hole cast in place while fabricating the matrix to accommodate the axial terminal.

For sintered ceramics, in one embodiment, before applying the conductive adhesive, a reservoir is drilled onto the sensor matrix surface to hold part of the conductive adhesive materials and act as an anchor against shearing. In one embodiment, the cylindrical sensor body matrix has a hole drilled in after manufacturing to accommodate the axial terminal.

The part of the sensor matrix that is attached to the terminals and wires is packaged in an insulating enclosure, preventing current leakage. This enclosure does not cover other parts of the sensor matrix as they need to be in contact with the surrounding concrete and reach equilibrium with the concrete pore solution. In one embodiment, the insulating enclosure is electrical-, water-, and chemical-resistant, strong, and durable in a high pH environment.

The insulating enclosure can be made using various techniques. In one embodiment, encapsulant epoxies are cast into the required shape and complexity to encapsulate the sensor, serving both as insulation and a package shape that is compatible with the placement mechanism. In one embodiment, the interface between the exposed portion of the sensor's matrix and the insulated part can be treated with a hermetic sealant preventing fluids infiltration inside the assembly. In one embodiment, a spray-on liquid insulation can be used in multiple layers. In this case, the insulation and placement mechanisms are separate. In one embodiment, heat shrinking insulating plastic can be used to insulate and hold terminals and wiring in place. In this case, the insulation and placement mechanisms are separate.

Sensor Packaging and Placement

The sensor placement mechanism is designed in a way that would be easily embedded in concrete cylinders or concrete structures. It should be appreciated that any use of the term structure is not limiting in volume or shape. In one embodiment, the sensor will be inserted inside a circular plug (FIG. 3 and FIG. 4) which is then attached to a sensor-holding frame by inserting it in place and twisting (FIG. 6). Any mechanism of engagement of the housed sensor into a holding frame may be used. In one embodiment, the sensor is inserted inside a plastic cage with square openings (e.g., 5 by 5 mm). In one embodiment, the cage will include a thermocouple and a relative humidity sensor. In one embodiment, the plastic cage will include an elastic strap (tie band) that will facilitate attachment of the sensor assembly to the plastic chairs (stands) used for holding steel reinforcement in place ahead of pouring concrete.

The required parts for both placement mechanisms can be fabricated using either 3D printing with resins and plastics, or injection molding of plastics. In one embodiment, the sensor assembly/package is shipped preassembled and pre-saturated in a simulated pore solution to promote shorter time to chemical equilibrium after placed inside concrete. In one embodiment, the pre-saturated sensor assembly can be shipped inside a shipping container filled with a simulated pore solution to ensure it remains saturated during shipping (FIG. 5). In one embodiment, the sensor assembly is saturated in the simulated pore solution and then shipped in a vacuum sealed package. In one embodiment, the simulated pore solution concentration must be no more than 20% different from the concentration of the pore solution in typical concrete materials. In one embodiment, sensor will be calibrated with this simulated pore solution before shipping.

Electrical Leads

In one embodiment, the electrical leads (wires) connect to an internal power source, such as a battery. In one embodiment, the battery is positioned within the sensor housing. In one embodiment, the battery is positioned outside the sensor housing. In one embodiment, the battery is attached to the inside surface or the outside surface of the sensor housing. In one embodiment, the battery extends through the sensor housing. In one embodiment, such as when the sensor comprises a battery, electrical leads do not extend beyond the sensor. In one embodiment, electrical leads do not extend outside the concrete sample (e.g., cylinder) or structure.

In one embodiment, the electrical leads connected to the first electrode and the second electrode extend outside the sensor housing. In some embodiments, the electrical leads are of sufficient length to extend outside of concrete samples or structures in which the sensor will be embedded. In one embodiment, the electrical leads connect to an external power source, such as a photovoltaic cell, a concentrator cell, a thermovoltaic cell, a piezoelectric cell, a fuel cell, an electrochemical cell, a radioisotope thermal generator, a micro wind turbine, or any power source.

In one embodiment, the sensor further comprises means for transporting a signal outside the sensor. In one embodiment, the sensor comprises a Bluetooth transmitter, a wireless transmitter, a wired transmitter, or the like, so as to transfer data between the sensor and an external receiver.

In some embodiments of the present invention, the electrical leads are coated with any of a metal oxide, a polymer, or any combination thereof. In one embodiment, the electrical leads are coated with an epoxy coating.

Sensor Housing and Framework

As described previously, the sensors described herein may be further integrated into any desired housing framework or system, for example for use in concrete samples or structures. The sensor housing protects the sensor from the external strain of any surrounding cementitious material or similar environs. Exemplary embodiments include the housing designs described and depicted in FIGS. 3 and 4, and further their integration into the exemplary framework described and depicted in FIGS. 6 and 7. It is to be noted that although example housing and enclosures are disclosed within the present invention, the size or shape of the housing or enclosure is not limited in size or shape. Housing and framework components may be composed of polymeric materials, or any other materials suitable for embedding in concrete.

Computing Device

Figure 8:
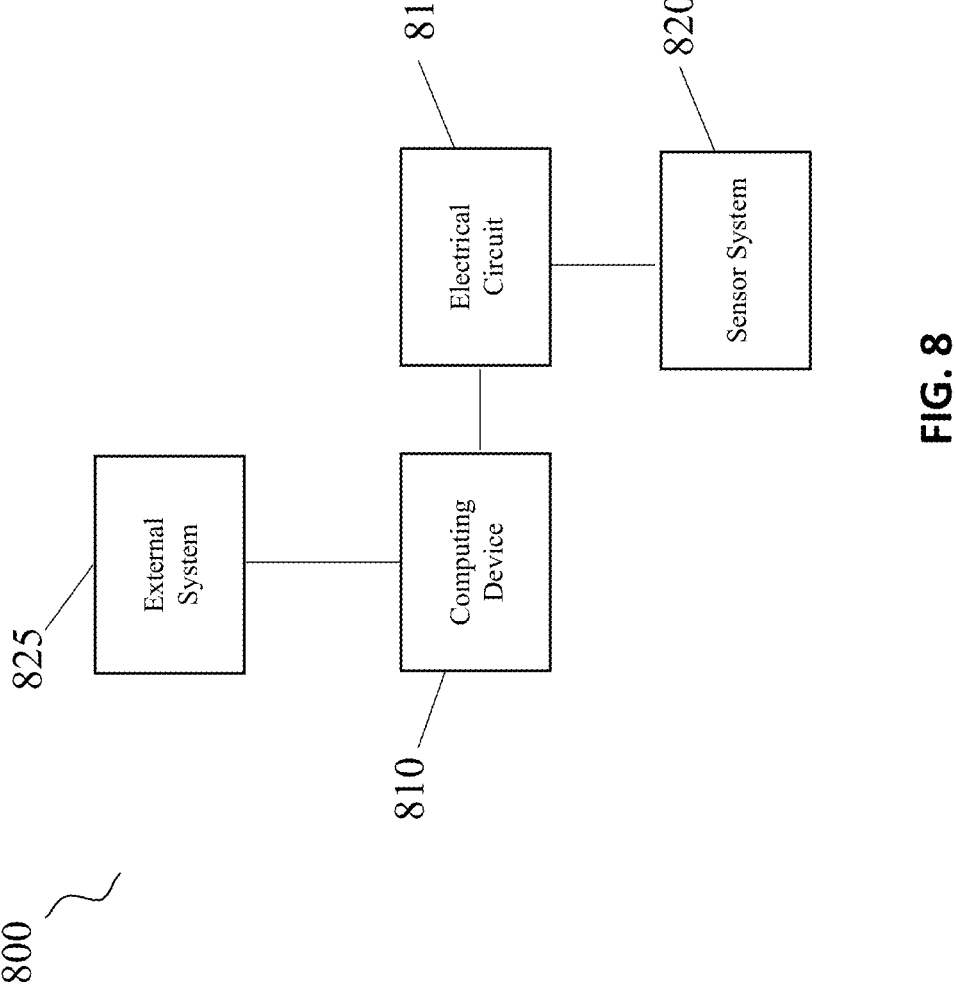
FIG. 8 is an exemplary diagram of a sensor interrogation schematic according to an aspect of the present invention.

Aspects of this invention relate to a computing device for controlling and enabling functions within the system. In one aspect, the present invention relates to the electrical control of the system described herein. In one embodiment, the system 600 comprises a computing device 810 from FIG. 8. In one embodiment, the computing device 810 is the computing device 900 from FIG. 9. In one embodiment, the computing device 810 is any of the "Example Interrogation Devices" listed above. In one embodiment, the computing device 810 is powered via an electrical power source. In one embodiment, the computing device 810 is connected to one or more sensor systems 820. In one embodiment, sensor system 820 is sensor system 300 or sensor system 400. In one embodiment, the computing device 810 is connected to one or more sensor systems 820 with lead wires. In one embodiment, the computing device 810 is capable of controlling electrical current to the sensor system 820. In one embodiment, the computing device 810 is capable of receiving an electrical signal from the sensor system 820. In one embodiment the computing device 810 is capable of processing an electrical signal from the sensor system 820. In one embodiment the computing device 810 is capable of recording and storing an electrical signal from the sensor system 820. In one embodiment the computing device 810 is capable of reporting the stored electrical signal from the sensor system 820 to an external system 825 and/or operator of system.

In one aspect, the present invention relates to a computing device 810 with electrical circuitry 815 for enabling the invention described herein. In one embodiment, the computing device 810 comprises an electrical circuit 815 with electrical components. In one embodiment the electrical circuit 815 is forming a connection between a computing system 810 and one or more sensor systems 820. In one embodiment, the electrical circuit 815 is producing electrical current sent to the sensor systems 820. In one embodiment, the electrical circuit 815 comprises active electronic components including, but not limited to transistors, silicon-controlled rectifiers (SCRs), diodes and/or semiconductor devices. In one embodiment, the electrical circuit 815 comprises passive electronic components including, but not limited to, resistors, capacitors, inductors and/or transformers. In one embodiment, the electrical circuit 815 comprises one or more voltage converters. In one embodiment, the electrical circuit 815 comprises one or more voltage inverters. In one embodiment, the electrical circuit 815 comprises one or more operational amplifiers (OPAMPS). In one embodiment the electrical circuit 815 is amplifying a signal received from the sensor system 820. In one embodiment, the electrical circuit 815 is performing signal filtering on one or more signals received from sensor system 820. In one embodiment the electrical circuit 815 is performing mathematical computations on one or more signals received from the electrodes.

In one aspect, the present invention relates to an electrical circuit 815 for processing the signals produced by the one or more electrodes. An operational amplifier (op amp) can be used in a number of ways to process a signal. In one embodiment, an operational amplifier (OPAMP) is used to calculate the voltage differential between the electrodes. In one embodiment, an operational amplifier (OPAMP) is used to calculate the conductance between the electrodes. In one embodiment, an operational amplifier (OPAMP) is used to calculate the impedance between the electrodes. In one embodiment, an operational amplifier (OPAMP) is used to create a voltage offset for one or more of the signals produced by the electrodes. In one embodiment, an operational amplifier (OPAMP) is used as a low-pass, high-pass, band-pass and/or band-stop filter to filter the signals produced by the electrodes. In one embodiment, an operational amplifier (OPAM) is used to reduce or eliminate Electromagnetitic interference (EMI). In one embodiment, an operational amplifier (OPAM) and a combination of capacitors and/or resistors are used to amplify the desired signal region. In one embodiment, an operational amplifier (OPAM) and a combination of capacitors and/or resistors are used to filter and/or remove unwanted electrical signal frequencies. In one embodiment, an operational amplifier (OPAM) and a combination of capacitors and/or resistors are used to and reduce and/or eliminate Electro-magnetitic interference (EMI) from common power sources such as 120/220V AC power.

In one aspect, the present invention relates to a computing device 810 with operational software enabling the invention described herein. In one embodiment, the computing device 810 of the system comprises a software executing the instructions provided herein may be stored on a non-transitory computer-readable medium, wherein the software performs some or all of the steps of the present invention when executed on a processor. In one embodiment, the computing device 810 comprises a software executing the necessary steps for analog to digital conversion of one or more electrical signals. In one embodiment, the software correlates the electrical signals to spatial data of the system. In one embodiment, the software correlates the electrical signals to temporal data of the system. In one embodiment, the software correlates the system, signals and data to a geo-location. In one embodiment, the computing device 810 comprises a software executing the steps for producing a user interface for a graphical representation of the system data.

Aspects of the invention relate to algorithms executed in computer software. Though certain embodiments may be described as written in particular programming languages, or executed on particular operating systems or computing platforms, it is understood that the system and method of the present invention is not limited to any particular computing language, platform, or combination thereof. Software executing the algorithms described herein may be written in any programming language known in the art, compiled or interpreted, including but not limited to C, C++, C #, Objective-C, Java, JavaScript, MATLAB, Python, PHP, Perl, Ruby, or Visual Basic. It is further understood that elements of the present invention may be executed on any acceptable computing platform, including but not limited to a server, a cloud instance, a workstation, a thin client, a mobile device, an embedded microcontroller, a television, or any other suitable computing device known in the art.

Parts of this invention are described as software running on a computing device. Though software described herein may be disclosed as operating on one particular computing device (e.g. a dedicated server or a workstation), it is understood in the art that software is intrinsically portable and that most software running on a dedicated server may also be run, for the purposes of the present invention, on any of a wide range of devices including desktop or mobile devices, laptops, tablets, smartphones, watches, wearable electronics or other wireless digital/cellular phones, televisions, cloud instances, embedded microcontrollers, thin client devices, or any other suitable computing device known in the art.

Similarly, parts of this invention are described as communicating over a variety of wireless or wired computer networks. For the purposes of this invention, the words "network", "networked", and "networking" are understood to encompass wired Ethernet, fiber optic connections, wireless connections including any of the various 802.11 standards, cellular WAN infrastructures such as 3G, 4G/LTE, or 5G networks, Bluetooth®, Bluetooth® Low Energy (BLE) or Zigbee® communication links, or any other method by which one electronic device is capable of communicating with another. In some embodiments, elements of the networked portion of the invention may be implemented over a Virtual Private Network (VPN).

Computing Environment

Figure 9:
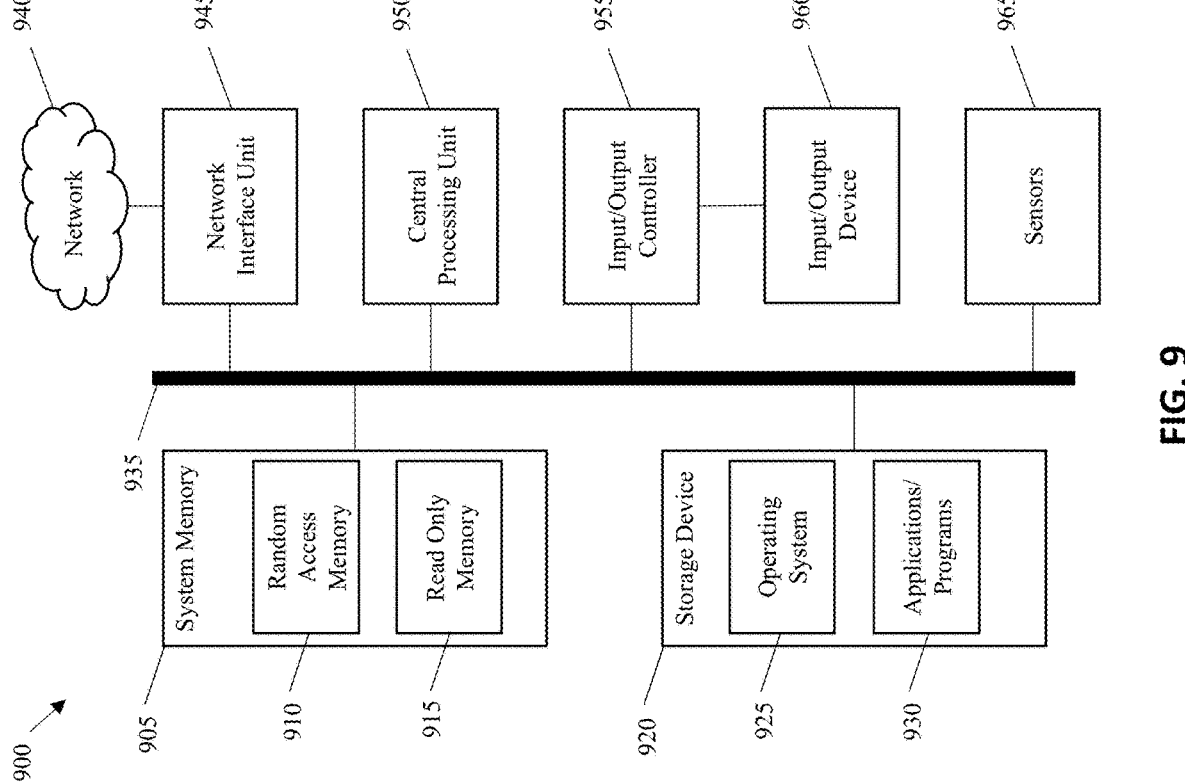
FIG. 9 is an exemplary diagram of a computing device according to an aspect of the present invention.

FIG. 9 and the following discussion are intended to provide a brief, general description of a suitable computing environment in which the invention may be implemented. While the invention is described above in the general context of program modules that execute in conjunction with an application program that runs on an operating system on a computer, those skilled in the art will recognize that the invention may also be implemented in combination with other program modules.

Generally, program modules include routines, programs, components, data structures, and other types of structures that perform particular tasks or implement particular abstract data types. Moreover, those skilled in the art will appreciate that the invention may be practiced with other computer system configurations, including hand-held devices, multiprocessor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote memory storage devices.

FIG. 9 depicts an illustrative computer architecture for a computer 900 for practicing the various embodiments of the invention. The computer architecture shown in FIG. 9 illustrates a conventional personal computer, including a central processing unit 950 ("CPU"), a system memory 905, including a random access memory 910 ("RAM") and a read-only memory ("ROM") 915, and a system bus 935 that couples the system memory 905 to the CPU 950. A basic input/output system containing the basic routines that help to transfer information between elements within the computer, such as during startup, is stored in the ROM 915. The computer 900 further includes a storage device 920 for storing an operating system 925, application/program 930, and data.

The storage device 920 is connected to the CPU 950 through a storage controller (not shown) connected to the bus 935. The storage device 920 and its associated computer-readable media provide non-volatile storage for the computer 900. Although the description of computer-readable media contained herein refers to a storage device, such as a hard disk or CD-ROM drive, it should be appreciated by those skilled in the art that computer-readable media can be any available media that can be accessed by the computer 900.

By way of example, and not to be limiting, computer-readable media may comprise computer storage media. Computer storage media includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

According to various embodiments of the invention, the computer 900 may operate in a networked environment using logical connections to remote computers through a network 940, such as TCP/IP network such as the Internet or an intranet. The computer 900 may connect to the network 940 through a network interface unit 945 connected to the bus 935. It should be appreciated that the network interface unit 945 may also be utilized to connect to other types of networks and remote computer systems.

The computer 900 may also include an input/output controller 955 for receiving and processing input from a number of input/output devices 960, including a keyboard, a mouse, a touchscreen, a camera, a microphone, a controller, a joystick, or other type of input device. Similarly, the input/output controller 955 may provide output to a display screen, a printer, a speaker, or other type of output device. The computer 900 can connect to the input/output device 960 via a wired connection including, but not limited to, fiber optic, Ethernet, or copper wire or wireless means including, but not limited to, Wi-Fi, Bluetooth, Near-Field Communication (NFC), infrared, or other suitable wired or wireless connections.

As mentioned briefly above, a number of program modules and data files may be stored in the storage device 920 and/or RAM 910 of the computer 900, including an operating system 925 suitable for controlling the operation of a networked computer. The storage device 920 and RAM 910 may also store one or more applications/programs 930. In particular, the storage device 920 and RAM 910 may store an application/program 930 for providing a variety of functionalities to a user. For instance, the application/program 930 may comprise many types of programs such as a word processing application, a spreadsheet application, a desktop publishing application, a database application, a gaming application, internet browsing application, electronic mail application, messaging application, and the like. According to an embodiment of the present invention, the application/program 930 comprises a multiple functionality software application for providing word processing functionality, slide presentation functionality, spreadsheet functionality, database functionality and the like.

The computer 900 in some embodiments can include a variety of sensors 965 for monitoring the environment surrounding and the environment internal to the computer 900. These sensors 965 can include a Global Positioning System (GPS) sensor, a photosensitive sensor, a gyroscope, a magnetometer, thermometer, a proximity sensor, an accelerometer, a microphone, biometric sensor, barometer, humidity sensor, radiation sensor, or any other suitable sensor.

Methods of the Invention

In one aspect, the present invention relates to a method of determining the conductivity or resistivity of a concrete pore solution, the method comprising the steps of embedding a sensor described herein in a concrete sample or concrete structure and measuring the conductivity or resistivity of a pore solution in the concrete. It should be appreciated that any use of the term sample or structure is not limiting in volume or shape.

In one embodiment, the sensor further comprises a device for measuring the internal temperature and relative humidity of the concrete sample or structure. In one embodiment, the measurement of pore solution resistivity may be used to calculate the formation factor of the concrete sample or structure.

In one embodiment, the sensor is pre-calibrated by saturating with various salt solutions of known electrical conductivity. This allows quantifying surface conduction effects. In one embodiment, the sensor is pre-saturated with a simulated pore solution before embedding inside concrete.

EXPERIMENTAL EXAMPLES

The present invention involves a commercially viable concrete pore solution resistivity (PSR) sensor. In line with the Performance Engineered Mixtures (PEM) initiative, a concrete's Formation Factor (F) is used to assess its transport properties and as an indicator of its long-term durability. The F factor has been shown to be an important parameter in service-life models to predict chloride ion penetration and corrosion and permeability of concrete. In AASHTO PP 84-20, the F factor is defined as the ratio of the electrical resistivity of the bulk concrete mixture over the resistivity of the concrete pore solution. The AASHTO TP 119-21 and the equivalent ASTM C1876-19 standards were developed to measure the bulk concrete resistivity, and AASHTO T 358 to measure surface resistivity of the concrete mixture.

However, there are no standard equipment or test methods for non-destructive measurement of the pore solution resistivity, and the only available methods involve labor-intensive laboratory extraction of the pore solution. In-situ measurement of the electrical resistivity of the pore solution along with the resistivity of bulk concrete allows for qualification of concrete mix designs before construction, for quality control (QC) and quality acceptance (QA) of concrete placed during construction, and for service-life prediction of vital concrete infrastructure such as bridges, pavements, and marine structures. Additionally, the PSR sensor can be embedded in structures and used for long-term health monitoring to evaluate changes in the chloride content inside concrete over time. Finally, the sensor's output can be translated to concrete's internal pH and used for evaluation and mitigation of the risk of alkali-silica reaction (ASR) in concrete containing reactive aggregates.

The technology is a sensor system that allows in-situ measurement of concrete's PSR with a high accuracy compared to laboratory measurements of extracted pore solution, and a high level of repeatability and reproducibility. The sensor system includes the sensor assembly that is embedded inside concrete and a measuring device to interrogate the sensor. The sensor assembly includes the sensor matrix, attached insulated electrodes and leads, and a placement mechanism. The sensor matrix is made of custom-designed nano-porous materials with controlled porosity, pore size, and formation factor. The sensor placement mechanism is designed in a way that would be easily embedded in concrete samples or structures. The mobile measurement device is a low-cost consumer-level product. The overall sensor system and the simple data post-processing is designed for seamless application by field and lab technicians, ideally along with the bulk or surface resistivity measurements.

The electrical resistance of concrete can be simply measured by applying a known voltage between two electrodes that are embedded inside concrete or properly placed on the surface of concrete and measuring the resulting electrical current (F. Rajabipour, 2006, Ph.D. Dissertation, Purdue University). Methods for both two- and four-electrode measurements as well as direct current (DC) and alternating current (AC) measurements are available (American Association of State and Highway Transportation Officials (2019) "AASHTO T 358-19: Standard method of test for surface resistivity indication of concrete's ability to resist chloride ion penetration."; American Association of State and Highway Transportation Officials (2015) "AASHTO TP 119-15: Standard method of test for electrical resistivity of a concrete cylinder tested in a uniaxial resistance test.")). AC measurements provide advantages such as faster and more stable and repeatable readings, eliminating the electrical polarization, and the use of smaller voltages that cause less perturbation to surrounding concrete (F. Rajabipour, J. Weiss, ACI Special Publication: SP 252-1, 2008, American Concrete Institute (ACI)).

The measured electrical resistance is converted to electrical resistivity or conductivity by applying a geometry factor to normalize the influence of electrodes' and specimen's geometry (F. Rajabipour, Ph.D. Dissertation, 2006, Purdue University, West Lafayette, Indiana):

$$\sigma = \frac{1}{\rho} = \frac{k_g}{R} \tag{Eq. 1}$$

where $\sigma$ (S/m) is the conductivity of concrete, $\rho$ ($\Omega$m) is the resistivity (inverse of conductivity) of concrete, R ($\Omega$) is the measured electrical resistance, and $k_g$ (1/m) is a geometry factor that can be measured experimentally (F. Rajabipour, Ph.D. Dissertation, 2006, Purdue University, West Lafayette, Indiana). Concrete is a porous material with pore sizes in the range of a few nanometers to tens of micrometers that are filled with an ionic aqueous pore solution. While the solid and gas (air void) phases in concrete are practically electrically insulating, the ionic pore solution is a good conductor of electricity (F. Rajabipour, Ph.D. Dissertation, 2006, Purdue University, West Lafayette, Indiana). As such, it has been shown that the electrical conductivity of concrete is a function of the pore solution conductivity, porosity, and pore connectivity as described by (BJ. Christensen, et al., Journal of the American Ceramic Society 1994, 77, 2789-2802; F. Rajabipour, J. Weiss "Electrical conductivity of drying cement paste," Materials and Structures 2007, 40, 1143-1160):

$$\sigma = \sigma_o \phi \beta = \frac{\sigma_o}{F} \tag{Eq. 2}$$

where $\sigma_o$ (S/m) is the pore solution conductivity, $\phi$ (unitless) is the volume fraction of pore solution (i.e., liquid filled porosity), $\beta$ (unitless) is the pore solution connectivity (i.e., it accounts for the effective length and constrictions of the liquid-filled pores), and F is the formation factor which lumps the effects of the material's microstructure on its electrical conductivity (FAL. Dullien (1991) "Porous media: Fluid transport and pore structure," 2nd Ed., Academic Press, New York). Eq. 2 can be similarly written in resistivity terms as below where $\rho_o$ ($\Omega$m) is the resistivity of pore solution:

$$\rho = \rho_o F \qquad \text{(Eq. 3)}$$

As such, by simultaneous measurements of the conductivity (or resistivity) of concrete and the conductivity (or resistivity) of pore solution, the formation factor (F) of concrete can be obtained. The F factor can be directly used to qualitatively assess the chloride ion penetrability of concrete as negligible, very low, low, moderate, or high as per AASHTO PP84-20 (American Association of State and Highway Transportation Officials (2020) "AASHTO PP 84-20: Standard practice for developing performance engineered concrete pavement mixtures."). Chloride penetrability significantly impacts the life expectancy and durability of concrete against corrosion of reinforcing steel. Additionally, important mass transport properties of concrete (such as ion diffusivity and water permeability) can be calculated using the measured formation factor (A. Atkinson, AK. Nickerson, Journal of Materials Science 1984, 19 3068-3078; AJ. Katz, AH. Thompson, Physical Review B 1986, 34, 8179-8181):

$$D = \frac{D_o}{F} \qquad \text{(Eq. 4)}$$

$$K = \frac{d_c^2}{226F} \qquad \text{(Eq. 5)}$$

where D (m$^2$/s) is the bulk ionic diffusivity of concrete (for a known penetrating substance such as dissolved NaCl salt), $D_o$ (m$^2$/s) is the diffusivity of that substance inside the pore solution (for NaCl, $D_o$=1.484×10$^{-9}$ m$^2$/s can be assumed (JR. Rumble (2020) "CRC handbook of chemistry and physics," 101st Ed., CRC Press, Taylor and Francis.)), K (m$^2$) is concrete's intrinsic permeability, and $d_c$ (m) is a characteristic pore size that controls permeability (AJ. Katz, AH. Thompson (1986) "Quantitative prediction of permeability in porous rock," Physical Review B, 34(11) 8179-8181).

Measuring the formation factor of concrete is a powerful tool both as a quality control and quality assurance (QC/QA) method to ensure that high quality concrete that is durable in a given exposure condition is delivered and built, and to calculate mass transport properties that allow quantitative prediction of the durability and service life of concrete. To determine the formation factor, simultaneous measurements of both concrete conductivity and pore solution conductivity are needed. While it may be possible to measure concrete conductivity using established standard methods, there are currently no methods available for rapid, repeatable, and non-destructive measurement of pore solution conductivity.

Previously, a sensor has been proposed to be made from natural siltstone with known pore structure and formation factor. This sensor would be embedded inside and be in direct contact with concrete. As such, the solution inside the sensor would reach chemical equilibrium with the pore solution of the surrounding concrete. By measuring the electrical conductivity of the sensor ($\sigma_S$) and knowing the sensor's formation factor ($F_S$), the pore solution conductivity of concrete ($\sigma_o$) is determined via Eq. (2).

However, several challenges exist that have prevented development of a commercial pore solution resistivity sensor including: identifying a natural material (e.g., siltstone) with desirable $F_s$ value; natural stones are variable in their porosity and formation factor, and as such, their $F_s$ value may not be constant, resulting in variability in the measured pore solution conductivity; natural stones are prone to physical and chemical alteration and degradation in concrete, affecting the sensor outputs; the sensor measurements may be affected by the internal relative humidity of concrete which is not easy to accurately measure; and previous sensor geometries are prone to leaking of the electrical current into the surrounding concrete hence reducing the sensor's precision and accuracy.

The sensor design disclosed herein addresses the above shortcomings and allows for rapid, reliable, and non-destructive measurements of pore solution conductivity of concrete.

The invention is now described with reference to the following Examples. These Examples are provided for the purpose of illustration only, and the invention is not limited to these Examples, but rather encompasses all variations that are evident as a result of the teachings provided herein.

The sensor matrix is made of a custom-designed nanoporous materials with controlled porosity, pore size, and formation factor. Example of such materials include but are not limited to autoclaved concrete, geopolymer, dry-pressed sintered alumina or mullite ceramics, or organic polymers.

In one embodiment, the sensor matrix comprises autoclaved concrete with water to cement (w/cm) ratio of 0.20, comprised of 700 grams of cement, 200 grams of silica flour, 100 grams of un-densified silica fume, 200 grams of water, and 4.5 milliliters of high-range water reducing admixture (HRWRA). Sensor body is autoclaved with maximum temperature of 180° C. and 125 psi pressure, ramp up period of about 1.5 hours, holding period of 3 hours at maximum temperature, and cooling period of about 30 minutes.

In one embodiment, the sensor matrix comprises dry-pressed alumina ceramics sintered under 115 MPa pressure and temperature of 1100° C. The alumina powder is first mixed with a small amount of isopropanol to achieve good compaction. The mix is then pressed into pellets under 115 MPa pressure and temperature of 1100° C.

In one embodiment, the sensor matrix comprises dry-pressed mullite ceramics sintered under 150 MPa pressure and temperature of 1285° C. β-alumina (40-80 nm average particle size) and silica (350 to 420 m$^2$/g) are combined in 3:2 molar ratio. Mechanical activation is essential for the formation of mullite at lower temperatures (1285° C.) by either hand grinding the components in a mortar and pestle or grinding the powder mixture with isopropanol in a micronizing mill with alumina grinding inserts for 15 minutes.

The sensor matrix shape can be one of the following embodiments, which are designed to minimize current leakage outside of the sensor and also minimize the time to achieve chemical equilibrium between the pore solution inside the sensor and the pore solution of the surrounding concrete.

One embodiment is a cuboidal membrane sensor (FIG. 3): for example, having 10 mm length by 10 mm width by 4 mm thickness; this sensor shape includes terminals on either side so that the current passes through the thickness (smallest dimension) of the sensor matrix.

Another embodiment is a cylindrical coaxial sensor (FIG. 4): for example, having 10 mm diameter by 10 mm height; this sensor shape includes one terminal as a belt around the sensor and another as an axial rod in the center of the cylinder.

The lead wires are attached to the terminals (electrodes) before attaching terminals to the sensor matrix. The terminals and wire are made of stainless steel, copper, titanium, or other conductive materials. The terminals are attached to the sensor matrix using conductive adhesives, which can be silver-filled two-component epoxy or polyurethane adhesives. The part of the sensor matrix that is attached to the terminals and wires is packaged in an insulating enclosure, preventing current leakage. This enclosure does not cover other parts of the sensor matrix as they need to be in contact with the surrounding concrete and reach equilibrium with the pore solution. The insulating enclosure is electrical-, water-, and chemical-resistant, strong, and durable in a high pH environment.

In one method, the encapsulant epoxies are cast into the required shape and complexity to encapsulate the sensor, serving both as insulation and a package shape that is compatible with the placement mechanism. The interface between the exposed portion of the sensor's matrix and the insulated part can be treated with a hermetic sealant preventing fluids infiltration inside the assembly. In another method, the spray-on liquid insulation can be used in multiple layers. In this case, the insulation and placement mechanisms are separate. In another method, heat shrinking insulating plastic can be used to insulate and hold terminals and wiring in place. In this case, the insulation and placement mechanisms are separate.

After attachment and insulation of the terminals and wires, the sensor is enclosed in a package for placement. The sensor placement mechanism is designed in a way that would be easily embedded in concrete samples (e.g., cylinders) or structures.

For placement inside cylindrical concrete samples, the sensor will be inserted inside a circular plug which can be attached to a sensor-holding frame by inserting it in place and twisting (FIG. 6). The frame also contains wiring used to interrogate the sensor and a protective dome designed to prevent damage to the sensor during concrete pouring and compaction. The size of the holding frame corresponds to the size of the standard cylindrical concrete molds, with diameter of 100 mm and height of 200 mm (4 by 8 inches) or diameter of 150 mm and height of 300 mm (6 by 12 inches). The frame itself is made 20 mm shorter than the cylinder height to allow some free space for the rolled lead wires to be stored under a sealed mold cap.

The sensor assembly/package is shipped preassembled and pre-saturated in a simulated pore solution to promote shorter time to chemical equilibrium after being placed inside concrete. The pre-saturated sensor assembly may be shipped inside a shipping container filled with a simulated pore solution to ensure it remains saturated during shipping (FIG. 5). Another alternative is to saturate the sensor in the simulated pore solution and then ship this assembly in a vacuum sealed package. The sensor is pre-calibrated by saturating with pore solution of known electrical conductivity to measure the precise formation factor of the sensor.

The test methodology using this sensor system includes placement of sensor inside cylindrical concrete samples or embedded in concrete structures, curing of the concrete, excitation of the sensor and acquisition of pertinent data. Conditioning of the concrete samples with embedded sensors can be done in saturated lime water, in simulated pore solution, or using sealed curing. For sensors embedded in concrete structures, normal curing operations could be conducted. The solution inside the sensor matrix will reach chemical/ionic equilibrium with the pore solution of the surrounding concrete within 14 days, when the interrogation process can be conducted.

For sensors placed in concrete samples, a set of commercially available interrogation devices are identified, which can excite the sensor at pertinent AC frequency ranges. These devices can be used both in a lab set-up and for field measurement.

A possible option for automatic data collection from sensors embedded in concrete structures is independent actuation of the sensor and wireless communication of the measurements to a data acquisition unit. As an alternative to automatic measurements, one or more sensors could be embedded inside a structure with lead wires (e.g., an electric plug) that are accessible from the surface of the structure. These sensors could be interrogated using a handheld device, which also serves as a power source.

The interrogator device will provide a measurement of the electrical resistivity for the sensor that is saturated with the pore solution of the surrounding concrete, adjusted for the known geometry factor of the sensor. The formation factor of the sensor matrix is known from the pre-calibration process at manufacturing facility. The measured electrical resistivity of the saturated sensor divided by the formation factor will result in the electrical resistivity of the concrete pore solution. These calculations will be programmed into the device so that the technician will read the final measurement.

Temperature significantly impacts the electrical resistivity measurements. This impact is limited for sensors placed in cylindrical concrete samples as they are typically tested in laboratory environments with a narrow range of temperatures. For sensors embedded in concrete structures, a thermocouple is included inside the sensor package for benchmarking the measurements to a reference temperature.

To ensure that the sensor's matrix remains nearly saturated at relative humidities pertinent to concrete interior (RH>80%), the sensor pore size is maintained below a threshold value (R) that can be calculated according to the Kelvin equation:

$$R = \frac{-2\gamma V_m \mathrm{Cos}\theta}{\mathcal{R}_g T \cdot \ln(RH/a_l)} \qquad \text{(Eq. 6)}$$

where R is the maximum pore radius, $\gamma$ is the surface tension of pore solution ($\approx 0.072$ N/m), $V_m$ is the molar volume of pore solution ($\approx 18 \times 10^{-6}$ m3/mol), $\theta$ is the liquid-solid contact angle at the pore wall (e.g., possibly $\theta \approx 0$ but can be experimentally verified based on the selected ceramic powder material), $\mathcal{R}g$ is the universal gas constant (=8.314 J/molK), T is the absolute temperature (K), and $a_l$ is the activity of water within the pore solution ($a_l \approx 1$). Assuming the above values and at temperature T=296 K, the maximum pore radius is determined as $R \approx 10$ nm for RH=90% and $R \approx 5$ nm for RH=80%.

Alternatively, the sensor can have larger pore sizes but is then coupled with an embedded relative humidity (RH) sensor to allow instant calibration of the pore solution sensor based on the measured RH inside concrete.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. A concrete pore solution resistivity/conductivity sensor comprising:
   a first electrode;
   a second electrode spaced from and opposite said first electrode, wherein the first electrode is configured to pass an alternating current to the second electrode; and
   a space between the first and second electrode that is occupied by a nanoporous matrix;
   said first and second electrodes being situated on a common axis or parallel axes and each having electrical leads connected thereto; and
   wherein said electrical leads extend through and outside the nanoporous matrix.

2. The resistivity/conductivity sensor of claim 1, wherein the first electrode has a cylindrical shape with a curved surface along its vertical extent that faces the second electrode; and
   the second electrode is a cylinder with a curved outer surface along its vertical extent.

3. The resistivity/conductivity sensor of claim 1, wherein the first electrode is a tubular shape and is embedded within the nanoporous matrix; and wherein the second electrode is positioned coaxially within a central region of the tubular first electrode.

4. The resistivity/conductivity sensor of claim 1, wherein the first electrode and the second electrode have a slab shape.

5. The resistivity/conductivity sensor of claim 1, wherein the nanoporous matrix has an average pore size not exceeding 20 nm in diameter.

6. The resistivity/conductivity sensor of claim 1, wherein the nanoporous matrix comprises a nanoporous ceramic.

7. The resistivity/conductivity sensor of claim 6, wherein the nanoporous matrix further comprises a monomolecular film coating.

8. The resistivity/conductivity sensor of claim 1, wherein the nanoporous matrix comprises a nanoporous polymer material.

9. The resistivity/conductivity sensor of claim 8, wherein the nanoporous polymer material comprises an ethylene-based polymer, a propylene-based polymer, an epoxy resin, a polyurethane, a silicone, an un-saturated ester, a phenolic resin, or combinations, mixtures, copolymers, and/or block copolymers thereof.

10. The resistivity/conductivity sensor of claim 8, wherein the nanoporous matrix further comprises a metal oxide coating.

11. The resistivity/conductivity sensor of claim 8, wherein the nanoporous matrix comprises a covalent organic framework.

12. The resistivity/conductivity sensor of claim 11, wherein the covalent organic framework is selected from the group consisting of COF-1, COF-5, COF-6, COF-8, COF-10, COF-11A, COF-14A, COF-16A, COF-18A, COF-42, COF-43, COF-66, COF-366, TP-COF, NiPc-PBBA COF, CTF-0, CTF-1, HTTP-DBP COF, ZnPc-Py COF, ZnPc-DPB COF, ZnPc-NDI COF, ZnPc-PPE COF, TpPa-1, or TpPa-2, TpPa-NO$_2$, TpBD-(NO$_2$)$_2$, TpBD-Me$_2$, TpPa-F$_4$, TpBD-OMe$_2$, TpBD, DhaTph COF, TAPB-TFP COF, iPrTAP-TFP, TAPB-TFPB, ILCOF-1, DAAQ-TFP COF, TAPB-PBA COF, HPB COF, HCB COF, H$_2$P-COF, Ph-An-COF, Tp-Azo COF, TP-PirDI COF, Py-Azine COF, CS COF, CuP-SQ COF, CuP-Ph COF, CuP-TFPh COF, Star-COF, CuPc-COF, CoPc-COF, NiPc BTDA COF, ZnP-COF, Ppy-COF, 1-S COF, 1-Se COF, 1-Te COF, T-COF 1, T-COF 2, T-COF 3, T-COF 4, NTU-COF-1, NTU-COF-2, APTES-COF-1, FCTF-1 COF, TRITER-1, TDCOF-5, BLP-2 COF, TpTP-H, TpTP-OEt, TpTP-OMEG, TpTP-ODEG, TpTP-OTEG, and combinations thereof.

13. The resistivity/conductivity sensor of claim 1, wherein the nanoporous matrix comprises a nanoporous autoclaved cementitious material; wherein the nanoporous cementitious material further comprises supplementary cementitious materials (SCM).

14. The resistivity/conductivity sensor of claim 1, where the nanoporous matrix comprises a geopolymer formed in exposure to water and alkaline chemicals from an aluminosilicate precursor material selected from the group consisting of metakaolin, calcined clay, natural pozzolan, volcanic ash, fly ash, ground bottom ash, and slag cement.

15. The resistivity/conductivity sensor of claim 1, further comprising a sensor for measuring internal temperature and relative humidity of concrete.

16. A concrete sample or concrete structure comprising the resistivity/conductivity sensor of claim 1.

17. A method for measuring the resistivity of a concrete pore solution, the method comprising the steps of:
   embedding the resistivity/conductivity sensor of claim 1 in a concrete sample or concrete structure;
   passing an alternating current from the first electrode to the second electrode;
   measuring the resistivity/conductivity sensor's electrical resistance between the first and second electrodes; and
   applying a known sensor calibration factor to determine the resistivity of concrete pore solution.

18. The resistivity/conductivity sensor of claim 1, further comprising:
   an encapsulating enclosure at least partially encapsulating the electrical leads, the first and second electrodes and the nanoporous matrix; and
   a sensor placement housing having an outer surface, wherein the resistivity/conductivity sensor and encapsulating enclosure are secured by the sensor placement housing such that the electrical leads and a surface of the nanoporous matrix are accessible from the outer surface of the sensor placement housing; and
   a holding frame having a sensor mounting region and at least one electrical lead, wherein the resistivity/conductivity sensor secured to the sensor placement housing engages the sensor mounting region such that the at least one electrical lead of the holding frame is electrically connected to the electrical leads of the resistivity/conductivity sensor.

19. The sensor of claim 14, wherein the nanoporous matrix has an average pore size not exceeding 20 nm in diameter.

20. A concrete pore solution resistivity/conductivity sensor comprising:
   a solid nanoporous matrix having an outer surface;
   a first electrode in contact with the nanoporous matrix;
   a first electrical lead in contact with the first electrode;
   a second electrode in contact with the nanoporous matrix;
   a second electrical lead in contact with the second electrode;
   wherein the first electrode is configured to pass an alternating current to the second electrode; and wherein the first and second electrodes are situated on a common axis or parallel axes; and wherein the first and second electrical leads are accessible from the outer surface of the nanoporous matrix.

* * * * *